US008815325B2

(12) United States Patent
David et al.

(10) Patent No.: US 8,815,325 B2
(45) Date of Patent: Aug. 26, 2014

(54) MEDICINAL INHALATION DEVICE

(75) Inventors: Moses M. David, Woodbury, MN (US); Daniel R. Hanson, New Richmond, WI (US); Philip A. Jinks, Loughborough (GB); Christopher G. Blatchford, Loughborough (GB); Vicki M. Lietzau, Hutchinson, MN (US); Jean A. Kelly, Woodbury, MN (US); Suresh Iyer, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/318,277

(22) PCT Filed: May 6, 2010

(86) PCT No.: PCT/US2010/033847
§ 371 (c)(1),
(2), (4) Date: Jan. 13, 2012

(87) PCT Pub. No.: WO2010/129753
PCT Pub. Date: Nov. 11, 2010

(65) Prior Publication Data
US 2012/0103330 A1    May 3, 2012

Related U.S. Application Data

(60) Provisional application No. 61/175,887, filed on May 6, 2009.

(51) Int. Cl.
*A61M 15/00* (2006.01)
*B05D 1/00* (2006.01)
*C23C 16/32* (2006.01)

(52) U.S. Cl.
CPC ............ *C23C 16/325* (2013.01); *A61M 15/009* (2013.01)
USPC .. 427/2.1; 427/387; 128/203.15; 128/203.12; 428/336; 428/447; 428/451

(58) Field of Classification Search
None
See application file for complete search history.

(56) References Cited

U.S. PATENT DOCUMENTS

| | | |
|---|---|---|
| 3,250,808 A | 5/1966 | Moore, Jr. et al. |
| 3,646,085 A | 2/1972 | Bartlett |
| 3,810,874 A | 5/1974 | Mitsch et al. |
| 4,980,196 A | 12/1990 | Yasuda et al. |
| 4,991,822 A | 2/1991 | Enke |
| 6,156,689 A | 12/2000 | Kimble et al. |
| 6,592,659 B1 | 7/2003 | Terrazas et al. |
| 6,696,157 B1 * | 2/2004 | David et al. ................... 428/408 |
| 6,878,419 B2 | 4/2005 | David et al. |
| 8,104,469 B2 | 1/2012 | Dams |
| 2005/0133025 A1 * | 6/2005 | Laiho et al. .............. 128/200.23 |
| 2008/0050600 A1 | 2/2008 | Fan et al. |
| 2010/0242958 A1 | 9/2010 | Jinks et al. |
| 2010/0247932 A1 | 9/2010 | Jinks et al. |
| 2010/0263667 A1 | 10/2010 | Jinks et al. |

FOREIGN PATENT DOCUMENTS

| | | |
|---|---|---|
| CA | 725747 | 1/1966 |
| EP | 0 497 204 | 8/1992 |
| EP | 0 642 992 | 3/1995 |
| EP | 1300433 | 4/2003 |
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 97/41729 | 11/1997 |
| WO | WO 97/42154 | 11/1997 |
| WO | WO 01/64273 | 9/2001 |
| WO | WO 01/64274 | 9/2001 |
| WO | WO 01/64275 | 9/2001 |
| WO | WO 01/64524 | 9/2001 |
| WO | WO 02/30498 | 4/2002 |
| WO | WO 02/47829 | 6/2002 |
| WO | WO 03/006181 | 1/2003 |
| WO | WO 03/024623 | 3/2003 |
| WO | WO 03/095009 | 11/2003 |
| WO | WO 2009/029435 | 3/2009 |
| WO | WO 2009/061891 | 5/2009 |
| WO | WO 2009/061895 | 5/2009 |
| WO | WO 2010/129758 | 11/2010 |
| WO | WO 2010/129783 | 11/2010 |

OTHER PUBLICATIONS

Chapman, B.; "Glow Discharge Processes—Sputtering and Plasma Etching"; John Wily & Sons, New York; 1980, p. 153 (3 total pgs).
Ooij, W.J. et al., "Plasma-polymerized coatings of trimethylsilane deposited on cold-rolled steel substrates—Part 2. Effect of deposition conditions on corrosion performance", Progress in Organic Coatings, vol. 25, 1995, pp. 319-337.

* cited by examiner

Primary Examiner — Cachet Sellman

(57) ABSTRACT

A medical inhalation device or a component thereof having a diamond-like glass coating comprising hydrogen and on a hydrogen free basis about 20 to about 40 atomic percent of silicon, greater than 39 atomic percent of carbon, and less than 33 down to and including zero atomic percent of oxygen.

15 Claims, 2 Drawing Sheets

MEDICINAL INHALATION DEVICE

CROSS REFERENCE TO RELATED APPLICATIONS

This application is a national stage filing under 35 U.S.C. 371 of PCT/US2010/033847, filed May 6, 2010, which claims priority to U.S. Provisional Patent Application No. 61/175,887, filed May 6, 2009, the disclosure of which is incorporated by reference in its/their entirety herein.

FIELD OF THE INVENTION

The present invention relates to medicinal inhalation devices and components for such devices as well as methods of making such devices and components.

BACKGROUND OF THE INVENTION

Medicinal inhalation devices, including pressurized inhalers, such as metered dose pressurized inhalers (MDIs), and dry powder inhalers (DPIs), are widely used for delivering medicaments.

Medicinal inhalation devices typically comprise a plurality of hardware components, (which in the case of a MDI can include for example gasket seals; metered dose valves (including their individual components, such as ferrules, valve bodies, valve stems, tanks, springs retaining cups and seals); containers; and actuators) as well as a number of internal surfaces which may be in contact with the medicinal formulation during storage or come in contact with the medicinal formulation during delivery. Often a desirable material for a particular component is found to be unsuitable in regard to its surface properties, e.g., surface energy, and/or its interaction with the medicinal formulation. For example, the relatively high surface energy of materials typically used in MDIs, e.g., acetal polymer for valve stems, or deep drawn stainless steels or aluminum for containers, can cause medicament particles in suspension formulations to adhere irreversibly to the surfaces of corresponding component(s), which has a consequent impact on the uniformity of medicinal delivery. Similar effects are also observed for DPIs. Other examples of potentially undesirable interactions between a component and the medicinal formulation may include enhanced medicament degradation; adsorption of medicament or permeation of a formulation constituent or extraction of chemicals from plastic materials. For DPIs often permeation and adsorption of ambient water pose issues. Also the use of materials having relatively high surface energy for certain components (e.g., metered dose valves and/or individual components thereof), may have undesirable effects for the operation of movable components of a medicinal inhalation device.

Various coatings have been proposed for particular components or surfaces of metered dose inhalers, see e.g., EP 642 992, WO 96/32099, WO96/32150, WO96/32151, WO 96/32345, WO 99/42154, WO 02/47829, WO03/024623; WO 02/30498, WO 01/64273; WO 01/64274; WO 01/64275; WO 01/64524; and WO 03/006181.

SUMMARY OF THE INVENTION

Although a number of different coatings have been proposed, there is an ongoing need for medicinal inhalation devices and components thereof having desirable surface properties (e.g., desirable barrier properties and/or substrate-surface passivation) in conjunction with desirable structural integrity over the lifetime of the device (e.g., adhesion, durability, robustness and/or resistance to degradation) as well as during initial manufacture of the device (e.g., robustness and/or resistance to cracking) of a coating system provided on said devices and components as well as methods of providing such medicinal inhalation devices and components.

In aspects of the present invention there is provided a method of making a medicinal inhalation device or a component of a medicinal inhalation device, said method comprising a step of forming by plasma deposition under ion bombardment conditions a non-metal coating on at least a portion of a surface of the medicinal inhalation device or a component of a medicinal inhalation device, respectively, wherein the formed non-metal coating is a diamond-like glass comprising hydrogen and on a hydrogen free basis about 20 to about 40 atomic percent of silicon, greater than 39 atomic percent of carbon, and less than 33 down to and including zero atomic percent of oxygen.

Additional aspects of the present invention include: devices and components made in accordance with aforesaid method.

Further aspects of the present invention include: a medicinal inhalation device or a component of a medicinal inhalation device comprising a diamond-like glass coating on at least a portion of a surface of the device or component, respectively, said diamond-like glass comprising hydrogen and on a hydrogen free basis about 20 to about 40 atomic percent of silicon, greater than 39 atomic percent of carbon, and less than 33 down to and including zero atomic percent of oxygen.

Aforesaid diamond-like glasses may be described as oxygen-lean to oxygen free diamond-like glasses where in every case the content of carbon is greater than the content of oxygen.

The application of such diamond-like glass coatings advantageously allows for the provision of a system on the surface(s) of said devices and components having desirable structural integrity and/or surface characteristics. Among other things, it has been found that such diamond-like glass coatings show desirable expansion-capabilities together with marked flexibility, such properties being generally, continually further enhanced as the oxygen content approaches zero. These properties have been found to be particularly advantageous e.g., in regard to aerosol containers and the manufacture of pressurized metered dose inhalers where conventional metered dose valves are crimped onto aerosol containers. Moreover such diamond-like glass coatings provided on an interior surface of such containers advantageously resist cracking upon crimping operations. In addition such diamond-like glass coatings may show desirable surface characteristics, in particular barrier and/or passivation characteristics. Further, such diamond-like glass coatings may also have advantageously low surface energies.

Medicinal inhalation devices and components (in particular medicinal inhalation devices comprising such components) in accordance with aspects of the invention show desirable surface properties in conjunction with very favorable structural integrity.

Due to the desirable properties of diamond-like glass coatings described herein, they are particularly advantageous for use as coatings in medicinal inhalation devices or components thereof either alone or alternatively as a coating onto which a composition comprising an at least partially fluorinated compound is applied or alternatively treating at least a portion of a surface of the diamond-like glass coating with fluorine-containing gas plasma.

The following define further embodiments of the invention.

The invention, in its various combinations, either in method or apparatus form, may also be characterized by the following embodiments:

Embodiment 1

A method of making a medicinal inhalation device or a component of a medicinal inhalation device comprising a step of forming by plasma deposition under ion bombardment conditions a non-metal coating on at least a portion of a surface of the device or the component, respectively, wherein the non-metal coating formed is a diamond-like glass comprising hydrogen and on a hydrogen free basis from about 20 to about 40 atomic percent of silicon, greater than 39 atomic percent of carbon, and less than 33 down to and including zero atomic percent of oxygen.

Embodiment 2

A method according to embodiment 1, wherein the diamond-like glass contains on a hydrogen free basis from about 20 to about 40 atomic percent of silicon, greater than 42 atomic percent of carbon, less than 30 down to and including zero atomic percent of oxygen Embodiment 3

A method according to embodiment 2, wherein the diamond-like glass contains on a hydrogen free basis from about 20 to about 40 atomic percent of silicon, greater than 45 atomic percent of carbon, less than 28 down to and including zero atomic percent of oxygen.

Embodiment 4

A method according to embodiment 3, wherein the diamond-like glass contains on a hydrogen free basis from about 20 to about 40 atomic percent of silicon, greater than 50 atomic percent of carbon, less than 25 down to and including zero atomic percent of oxygen Embodiment 5

A method according to embodiment 4, wherein the diamond-like glass contains on a hydrogen free basis from about 20 to about 40 atomic percent of silicon, greater than 50 atomic percent of carbon, less than 20 down to and including zero atomic percent of oxygen.

Embodiment 6

A method according to embodiment 5, wherein the diamond-like glass contains on a hydrogen free basis from about 20 to, but not including 40 atomic percent of silicon, greater than 60 atomic percent of carbon, less than 15 down to and including zero atomic percent of oxygen.

Embodiment 7

A method according to any one of the preceding embodiments, wherein, on a hydrogen-free basis the content of oxygen, in the diamond-like glass is zero up to and including about 12 atomic percent.

Embodiment 8

A method according to any one of the preceding embodiments, wherein, on a hydrogen-free basis, the content of silicon in the diamond-like glass is in the range from about 20 to about 35 atomic percent.

Embodiment 9

A method according to any one of the preceding embodiments, wherein the non-metal coating is substantially free of fluorine, in particular free of fluorine.

Embodiment 10

A method according to any one of the preceding embodiments, wherein the non-metal coating is substantially free of nitrogen, in particular free of nitrogen; and/or wherein the non-metal coating is substantially free of sulfur, in particular free of sulfur.

Embodiment 11

A method according to any one of the preceding embodiments, wherein prior to forming the non-metal coating, said surface of the device or the component, as applicable, is exposed to an oxygen or argon plasma, in particular an oxygen plasma, more particularly an oxygen plasma under ion bombardment conditions.

Embodiment 12

A method according to any one of the preceding embodiments, wherein the forming the non-metal coating comprises ionizing a gas comprising an organosilicon.

Embodiment 13

A method according to embodiment 12, wherein the organosilicon is selected from the group consisting of trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, bistrimethylsilylmethane, and mixtures thereof, in particular the organosilicon is selected from the group consisting of trimethylsilane, triethylsilane, tetramethylsilane, tetraethylsilane, hexamethylcyclotrisiloxane, bistrimethylsilylmethane, more particularly the organosilicon is tetramethylsilane or tetraethyloxysilane, most particularly tetramethylsilane Embodiment 14

A method according to embodiment 12 or embodiment 13, wherein during ionizing of said gas comprising said organosilicon, said gas further comprises oxygen gas, where the amount of oxygen gas is less than 35% on a molar basis in the said gas, in particular less than 30% on a molar basis in said gas; and/or wherein during ionizing of said gas comprising said organosilicon, said gas further comprises an oxygen gas and/or said gas comprises an organosilicon comprising oxygen and wherein the atomic ratio of oxygen (O) to silicon (Si) in said gas is equal to or less than 3:1, in particular equal to or less than 2.5:1, more particularly equal to or less than 1:1, most particularly equal to or less than 0.8:1.

Embodiment 15

A method according to embodiment 12 or embodiment 13, wherein during ionizing of said gas comprising said organosilicon, said gas is substantially free or free of an oxygen assist gas; and/or wherein during ionizing of said gas comprising said organosilicon, said gas is substantially free or free of oxygen-containing organo silicons.

Embodiment 16

A method according to any one of embodiments 12 to 15, wherein during ionizing of said gas comprising said organosilicon, the plasma power density is greater than 0.1 watts/square; and/or wherein during ionizing of said gas comprising said organosilicon, the flow density of said organosilicon is greater than 0.01 sccm/square cm; and/or wherein during ionizing of said gas comprising said organosilicon, the pressure at the surface to be coated is greater than 100 millitorr, in particular equal to or greater than 300 millitorr, more particularly in the range from 500 millitorr to 5000 millitorr.

Embodiment 17

A method according to any one of the preceding embodiments, wherein the non-metal coating formed on said surface has a thickness greater than 100 nm, in particular a thickness equal to or greater than 250 nm, more particularly a thickness greater than 550 nm; and/or the non-metal coating formed on said surface has a thickness equal to or less than 5000 nm, in particular a thickness equal to or less than 3500 nm, more particularly a thickness equal to or less than 2500 nm, most particularly a thickness equal to or less than 2000 nm.

Embodiment 18

A method according to any one of the preceding embodiments, wherein the non-metal coating formed on said surface of the device or said surface of the component of the device, as applicable, is covalently bonded to said surface.

Embodiment 19

A method according to any one of embodiments 1 to 18, wherein the method further comprises a step of:
exposing at least a portion of a surface of the formed non-metal coating to a fluorine-containing-gas plasma, in particular a fluorine-containing-gas plasma under ion bombardment conditions.

Embodiment 20

A method according to embodiment 19, wherein the fluorine-containing-gas-plasma comprises a fluorine-containing compound selected from the group consisting of fluorine (F2); nitrogentrifluoride ($NF_3$); sulfurhexafluoride ($SF_6$); silicontetrafluorine ($SiF_4$); phosphorustrifluoride ($PF_3$); carbon tetrafluoride ($CF_4$); perfluoroethane ($C_2F_6$); perfluoropropane ($C_3F_8$), perfluorobutane ($C_4F_{10}$) and perfluoropentane ($C_5F_{12}$) and their isomeric forms; hexafluoropropylene (HFP) trimer; 2,2,3-trifluoro-3-(trifluoromethyl)oxirane ($C_3F_6O$) and mixtures thereof.

Embodiment 21

A method according to any one of embodiments 1 to 18, wherein the method further comprises a step of:
applying to at least a portion of a surface of the non-metal coating a composition comprising an at least partially fluorinated compound.

Embodiment 22

A method according to embodiment 21, wherein said at least partially fluorinated compound comprises at least one functional group and said non-metal coating has at least one functional group, wherein the non-metal coating is provided with said at least one functional group during the forming step or after the forming step the formed non-metal coating is treated to provide the non-metal coating with said at least one functional group, and wherein the method further comprises a step of:
allowing at least one functional group of the at least partially fluorinated compound to react with at least one functional group of the non-metal coating to form a covalent bond.

Embodiment 23

A method according to embodiment 22, wherein said at least one functional group of the non-metal coating has an active hydrogen.

Embodiment 24

A method according to embodiment 23, wherein said at least one functional group of the non-metal coating having an active hydrogen is selected from the group consisting of a hydroxyl group (—OH) and a carboxyl group (—COOH), in particular a hydroxyl group (—OH).

Embodiment 25

A method according to any one of embodiments 22 to 24, wherein said at least one functional group of the non-metal coating is a silanol group (—Si—OH).

Embodiment 26

A method according to any one of embodiments 22 to 25, wherein the non-metal coating comprises a plurality of functional groups.

Embodiment 27

A method according to any one of embodiments 21 to 26, wherein prior to applying the composition comprising an at least partially fluorinated compound, the non-metal coating is exposed to an oxygen and/or water vapor plasma or a corona treatment, in particular an oxygen and/or water vapor plasma, more particularly an oxygen and/or water vapor plasma under ion bombardment conditions.

Embodiment 28

A method according to any one of embodiments 22 to 27, wherein said at least one functional group of the at least partially fluorinated compound has a hydrolyzable group.

Embodiment 29

A method according to any one of embodiments 22 to 28, wherein said at least one functional group of the at least partially fluorinated compound is a silane group, in particular a silane group comprising at least one hydrolyzable group, more particularly at least two hydrolyzable groups, and most particularly three hydrolyzable groups.

Embodiment 30

A method according to any one of embodiments 21 to 29, wherein said at least partially fluorinated compound comprises a polyfluoropolyether segment, in particular a perfluorinated polyfluoropolyether segment.

Embodiment 31

A method according to any one of embodiments 21 to 30, wherein said at least partially fluorinated compound comprises a perfluorinated polyfluoropolyether segment, wherein the repeating units of the perfluorinated polyfluoropolyether segment the number of carbon atoms in sequence is at most 6, in particular at most 4, more particularly at most 3 and most particularly at most 2.

Embodiment 32

A method according to any one of embodiments 21 to 31, wherein the at least partially fluorinated compound is a polyfluoropolyether silane, in particular a multifunctional polyfluoropolyether silane, and more particularly a difunctional polyfluoropolyether silane.

Embodiment 33

A method according to embodiment 32, wherein the composition comprises a monofunctional polyfluoropolyether silane and a multifunctional polyfluoropolyether silane, in particular a difunctional polyfluoropolyether silane; and/or wherein the polyfluoropolyether segment(s) of the polyfluoropolyether silane is (are) not linked to the functional silane group(s) via a functionality that includes a nitrogen-silicon bond or a sulfur-silicon bond.

Embodiment 34

A method according to embodiment 32 or embodiment 33, wherein the polyfluoropolyether segment(s) of the polyfluoropolyether silane is (are) linked to the functional silane group(s) via a functionality that includes a carbon-silicon bond.

Embodiment 35

A method according to embodiment 34, wherein the polyfluoropolyether segment(s) of the polyfluoropolyether silane is (are) linked to the functional silane group(s) via a —C(R)$_2$—Si functionality where R is independently hydrogen or a C$_{1-4}$ alkyl group, more particularly hydrogen.

Embodiment 36

A method according to embodiment 34, wherein the polyfluoropolyether segment(s) of the polyfluoropolyether silane is (are) linked to the functional silane group(s) via a —(CR$_2$)$_k$—C(R)$_2$—Si functionality where k is at least 2 and where R is independently hydrogen or a C$_{1-4}$ alkyl group, more particularly hydrogen.

Embodiment 37

A method according to any one of embodiments 32 to 35, wherein the polyfluoropolyether silane is of Formula Ia:

$$R_f[Q\text{-}[C(R)_2\text{—}Si(Y)_{3-x}(R^{1a})_x]_y]_z \quad \text{Ia}$$

wherein:
  $R_f$ is a monovalent or multivalent polyfluoropolyether segment;
  Q is an organic divalent or trivalent linking group;
  each R is independently hydrogen or a C$_{1-4}$ alkyl group;
  each Y is independently a hydrolyzable group;
  $R^{1a}$ is a C$_{1-8}$ alkyl or phenyl group;
  x is 0 or 1 or 2;
  y is 1 or 2; and
  z is 1, 2, 3, or 4.

Embodiment 38

A method according to embodiment 37, wherein the polyfluoropolyether segment, $R_f$, comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

Embodiment 39

A method according to embodiment 38, wherein n is an integer from 1 to 4 and wherein for repeating units including Z the number of carbon atoms in sequence is at most four, in particular wherein n is an integer from 1 to 3 and wherein for repeating units including Z the number of carbon atoms in sequence is at most three.

Embodiment 40

A method according to embodiment 38 or embodiment 39, wherein the polyfluoropolyether segment, $R_f$, comprises perfluorinated repeating units selected from the group consisting of —(C$_n$F$_{2n}$O)—, —(CF(Z)O)—, and combinations thereof; wherein n is 1 or 2 and Z is an —CF$_3$ group.

Embodiment 41

A method according to any one of embodiments 37 to 39, wherein z is 1 and $R_f$ is selected from the group consisting of C$_3$F$_7$O(CF(CF$_3$)CF$_2$O)$_p$CF(CF$_3$)—, CF$_3$O(C$_2$F$_4$O)$_p$CF$_2$—, C$_3$F$_7$O(CF(CF$_3$)CF$_2$O)$_p$CF$_2$CF$_2$, C$_3$F$_7$O(CF$_2$CF$_2$CF$_2$O)$_p$CF$_2$CF$_2$—, C$_3$F$_7$O(CF$_2$CF$_2$CF$_2$O)$_p$CF(CF$_3$)— and CF$_3$O(CF$_2$CF(CF$_3$)O)$_p$(CF$_2$O)X—, wherein X is CF$_2$—, C$_2$F$_4$—, C$_3$F$_6$—, or C$_4$F$_8$— and wherein the average value of p is 3 to 50.

Embodiment 42

A method according to any one of embodiments 37 to 39, wherein z is 2, and $R_f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)—, —CF$_2$O(C$_2$F$_4$O)$_p$CF$_2$—, —(CF$_2$)$_3$O $(C_4F_8O)_p(CF_2)_3$—, —$CF(CF_3)$—$(OCF_2CF(CF_3))_pO$—$C_tF_{2t}$—$O(CF(CF_3)CF_2O)_pCF(CF_3)$—, wherein t is 2, 3 or 4 and wherein m is 1 to 50, and p is 3 to 40, in particular wherein $R_f$ is selected from the group consisting of —$CF_2O(CF_2O)_m(C_2F_4O)_pCF_2$—, —$CF_2O(C_2F_4O)_pCF_2$—, and —$CF(CF_3)$—$(OCF_2CF(CF_3))_pO$—$(C_tF_{2t})$—$O(CF(CF_3)CF_2O)_pCF(CF_3)$—, and wherein t is 2, 3 or 4, and wherein the average value of m+p or p+p or p is from about 4 to about 24.

Embodiment 43

A method according to any one of embodiments 37 to 41, wherein Q is selected from the group consisting of —C(O)N(R)—$(CH_2)_k$—, —$S(O)_2N(R)$—$(CH_2)_k$—, —$(CH_2)_k$—, —$CH_2O$—$(CH_2)_k$—, —$C(O)S$—$(CH_2)_k$—, —$CH_2OC(O)N(R)$—$(CH_2)_k$—, and

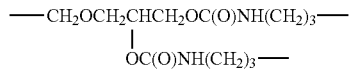

wherein R is hydrogen or $C_{1-4}$ alkyl, and k is 2 to about 25, in particular wherein Q is selected from the group consisting of —$C(O)N(R)(CH_2)_2$—, —$OC(O)N(R)(CH_2)_2$—, —$CH_2$—O—$(CH_2)_2$—, or —$CH_2$—$OC(O)N(R)$—$(CH_2)_2$—, wherein R is hydrogen or $C_{1-4}$ alkyl, and
y is 1.

Embodiment 44

A method according to any one of embodiments 35 to 43, wherein R is hydrogen.

Embodiment 45

A method according to any one of embodiments 37 to 44, wherein x is 0.

Embodiment 46

A method according to embodiment 28 or embodiment 29 or any one of embodiments 37 to 45, wherein each hydrolyzable group is independently selected from the group consisting of hydrogen, halogen, alkoxy, acyloxy, polyalkyleneoxy, and aryloxy groups, in particular wherein each hydrolyzable group is independently selected from the group consisting of alkoxy, acyloxy, aryloxy, and polyalkyleneoxy groups, more particularly wherein each hydrolyzable group is independently an alkoxy group, in particular an alkoxy group —OR' wherein each R' is independently a $C_{1-6}$ alkyl, more particularly a $C_{1-4}$ alkyl.

Embodiment 47

A method according to any one of embodiments 37 to 40 or any one of embodiments 42 to 46, wherein $R_f$ is —$CF_2O(CF_2O)_m(C_2F_4O)_pCF_2$—, and Q-C(R)$_2$—Si(Y')$_{3-x}$(R$^{1a}$)$_x$ is C(O)NH(CH$_2$)$_3$Si(OR')$_3$, and wherein m is 1 to 50 and p is 3 to 40, in particular wherein the average value of m+p or p is from about 4 to about 24, more particularly wherein m and p are each about 9 to about 12.

Embodiment 48

A method according to any one of embodiments 37 to 41 or any one of embodiments 43 to 46, wherein $R_f$ is $C_3F_7O$(CF(CF$_3$)CF$_2$O)$_p$CF(CF$_3$)—, and Q-C(R)$_2$—Si(Y')$_{3-x}$(R$_{1a}$)$_x$ is C(O)NH(CH$_2$)$_3$Si(OR')$_3$, and wherein p is 3 to 50, in particular wherein p is from about 3 to about 20, more particularly p is from about 4 to about 10.

Embodiment 49

A method according to embodiment 47 or embodiment 48, wherein R' is methyl or ethyl.

Embodiment 50

A method according to any one of embodiments 30 to 49, wherein the weight average molecular weight of the polyfluoropolyether segment is about 900 or higher, in particular about 1000 or higher; and/or the weight average molecular weight of the polyfluoropolyether segment is about 6000 or less, in particular about 4000 or less, more particularly about 3000 or less.

Embodiment 51

A method according to any one of embodiments 37 to 50, wherein the composition comprises at least the following two polyfluoropolyether silanes in accordance with Formula Ia:
(a) a first polyfluoropolyether silane wherein $R_f$ is $C_3F_7O$(CF(CF$_3$)CF$_2$O)$_p$CF(CF$_3$)—, and Q-C(R)$_2$—Si(Y')$_{3-x}$(R$_{1a}$)$_x$ is C(O)NH(CH$_2$)$_3$Si(OR')$_3$, wherein p is 3 to 50, in particular wherein p is from about 3 to about 20, more particularly p is from about 4 to about 10; and
(b) a second polyfluoropolyether silane wherein $R_f$ is —$CF_2O(CF_2O)_m(C_2F_4O)_pCF_2$—, and Q-C(R)$_2$—Si(Y')$_{3-x}$(R$^{1a}$)$_x$ is C(O)NH(CH$_2$)$_3$Si(OR')$_3$, wherein m is 1 to 50 and p is 3 to 40, in particular wherein the average value of m+p or p is from about 4 to about 24, more particularly wherein m and p are each about 9 to about 12.

Embodiment 52

A method according to embodiment 51, wherein R' is methyl or ethyl; and/or wherein either
the composition comprises a catalyst and the composition comprises at least a total of 0.1 wt % of said first and second polyfluoropolyether silanes, or
the composition is free of catalyst and the composition comprises at least a total of one (1) wt % of said first and second polyfluoropolyether silanes.

Embodiment 53

A method according to embodiment 51 or embodiment 52, wherein the weight percent ratio of the first to second polyfluoropolyether silane (first polyfluoropolyether silane:second polyfluoropolyether silane) in the composition is equal to or greater than 10:90, in particular equal to or greater than 20:80, more particularly equal to or greater than 30:70, most particularly equal to or greater than 40:60; and/or wherein the weight percent ratio of the first to second polyfluoropolyether silane (first polyfluoropolyether silane:second polyfluoropolyether silane) in the composition is equal to or less than 99:1, in particular equal to or less than 97:3, most particularly equal to or less than 95:5.

Embodiment 54

A method according to any one of embodiments 21 to 53, wherein the composition comprising an at least partially fluorinated compound further comprises an organic solvent, in particular an organic solvent that is a fluorinated solvent and/or a lower alcohol.

Embodiment 55

A method according to embodiment 54, wherein the composition comprising an at least partially fluorinated compound further comprises an acid.

Embodiment 56

A method according to any one of embodiments 21 to 55, wherein the composition comprising an at least partially fluorinated compound further comprises water and/or a non-fluorinated cross-linking agent, in particular a cross-linking agent comprising one or more non-fluorinated compounds, each compound having at least two hydrolyzable groups per molecule.

Embodiment 57

A method according to embodiment 56, wherein the composition comprises a non-fluorinated compound and the non-fluorinated compound is a compound in accordance to Formula II:

$$Si(Y^2)_{4-g}(R^5)_g \qquad \text{II}$$

where $R^5$ represents a non-hydrolyzable group;
$Y^2$ represents a hydrolyzable group; and
g is 0, 1 or 2.

Embodiment 58

A method according to embodiment 56 or embodiment 57, wherein the cross-linking agent comprises a compound selected from the group the consisting of tetramethoxysilane, tetraethoxysilane, tetrapropoxysilane, tetrabutoxysilane, methyl triethoxysilane, dimethyldiethoxysilane, octadecyltriethoxysilane, 3-glycidoxypropyltriethoxysilane, 3-aminopropyl-trimethoxysilane, 3-aminopropyltriethoxysilane, 3-trimethoxysilylpropylmethacrylate, and mixtures thereof.

Embodiment 59

A method according to any one of embodiments 21 to 58, wherein the composition comprising an at least partially fluorinated compound is applied by spraying, dipping, rolling, brushing, spreading, spin coating or flow coating, in particular by spraying or dipping; and/or wherein after applying the composition, the method further comprises a step of curing, in particular a step of curing at an elevated temperature in the range from about 40° C. to about 300° C.

Embodiment 60

A method according to any one of embodiments 1 to 18, wherein the method is free of a step of applying a fluorine-containing over-coating or a fluorine-containing surface-treatment onto the surface of the non-metal coating, in particular free of a step of applying an over-coating or a surface-treatment onto the surface of the non-metal coating.

Embodiment 61

A method according to any one of embodiments 1 to 60, where said surface of the device or said surface of the component of the device, as applicable, is a surface that is or will come in contact with a medicament or a medicinal formulation during storage or delivery from the medicinal inhalation device.

Embodiment 62

A method according to any one of embodiments 1 to 61, where said surface of the device or said surface of the component of the device, as applicable, is a surface that comes in contact with a movable component of the device or is a surface of a movable component of the device.

Embodiment 63

A method according to any one of embodiments 1 to 62, where said medicinal inhalation device is a metered dose inhaler or a dry powder inhaler.

Embodiment 64

A medicinal inhalation device or a component of a medicinal inhalation device made according to any one of embodiments 1 to 63.

Embodiment 65

A medicinal inhalation device or a component of a medicinal inhalation device comprising a diamond-like glass coating on at least a portion of a surface of the device or the component, respectively, said diamond-like glass comprising hydrogen and on a hydrogen free basis about 20 to about 40 atomic percent of silicon, greater than 39 atomic percent of carbon, and less than 33 down to and including zero atomic percent of oxygen.

Embodiment 66

A device or a component according to embodiment 65, wherein the diamond-like glass contains on a hydrogen free basis from about 20 to about 40 atomic percent of silicon, greater than 42 atomic percent of carbon, less than 30 down to and including zero atomic percent of oxygen

Embodiment 67

A device or a component according to embodiment 66, wherein the diamond-like glass contains on a hydrogen free basis from about 20 to about 40 atomic percent of silicon, greater than 45 atomic percent of carbon, less than 28 down to and including zero atomic percent of oxygen.

Embodiment 68

A device or a component according to embodiment 67, wherein the diamond-like glass contains on a hydrogen free basis from about 20 to about 40 atomic percent of silicon, greater than 50 atomic percent of carbon, less than 25 down to and including zero atomic percent of oxygen

Embodiment 69

A device or a component according to embodiment 68, wherein the diamond-like glass contains on a hydrogen free basis about 20 to about 40 atomic percent of silicon, greater than 50 atomic percent of carbon, less than 20 down to and including zero atomic percent of oxygen.

Embodiment 70

A device or a component according to embodiment 69, wherein the diamond-like glass contains on a hydrogen free basis about 20 to, but not including 40 atomic percent of silicon, greater than 60 atomic percent of carbon, less than 15 down to and including zero atomic percent of oxygen.

Embodiment 71

A device or a component according to any one of embodiments 65 to 70, wherein, on a hydrogen-free basis the content of oxygen, in the diamond-like glass is zero up to and including about 12 atomic percent.

Embodiment 72

A device or a component according to any one of embodiments 65 to 71, wherein, on a hydrogen-free basis, the content of silicon in the diamond-like glass is in the range from about 20 to about 35 atomic percent.

Embodiment 73

A device or a component according to any one of embodiments 65 to 72, said coating being plasma deposited under ion bombardment conditions; and/or wherein the diamond-like glass coating is covalently bonded to the at least a portion of a surface of the device or the component, respectively.

Embodiment 74

A device or a component according to any one of embodiments 65 to 73, wherein the diamond-like glass coating has a micro-hardness as determined using a nanoindenter of at least 1 GPa, in particular at least 2 GPa; and/or wherein the diamond-like glass coating has a micro-elastic-modulus as determined using a nanoindenter of less than 11 GPa.

Embodiment 75

A device or a component according to any one of embodiments 65 to 74, wherein the diamond-like glass coating on said surface has a thickness greater than 100 nm, in particular a thickness equal to or greater than 250 nm, more particularly a thickness greater than 550 nm; and/or the diamond-like glass coating on said surface has a thickness equal to or less than 5000 nm, in particular a thickness equal to or less than 3500 nm, more particularly a thickness equal to or less than 2500 nm, most particularly a thickness equal to or less than 2000 nm.

Embodiment 76

A device or a component according to any one of embodiments 65 to 75, wherein the diamond-like glass coating is substantially free of fluorine, in particular free of fluorine; and/or wherein the diamond-like glass coating is substantially free of nitrogen and/or sulfur, in particular free of nitrogen and/or sulfur.

Embodiment 77

A device or a component according to any one of embodiments 65 to 76, said diamond-like glass coating being post-treated with a fluorine-containing gas plasma, in particular a fluorine-containing-gas plasma under ion-bombardment conditions.

Embodiment 78

A device or a component according embodiment 77, said diamond-like glass coating being post-treated with a fluorine-containing gas plasma, said fluorine-containing-gas-plasma comprising a fluorine-containing compound selected from the group consisting of fluorine (F2); nitrogentrifluoride ($NF_3$); sulfurhexafluoride ($SF_6$); silicontetrafluorine ($SiF_4$); phosphorustrifluoride ($PF_3$); carbon tetrafluoride ($CF_4$); perfluoroethane ($C_2F_6$); perfluoropropane ($C_3F_8$), perfluorobutane ($C_4F_{10}$) and perfluoropentane ($C_5F_{12}$) and their isomeric forms; hexafluoropropylene (HFP) trimer; 2,2,3-trifluoro-3-(trifluoromethyl)oxirane ($C_3F_6O$) and mixtures thereof.

Embodiment 79

A device or a component according to any one of embodiments 65 to 76, wherein said device or component, respectively further comprises a fluorine-containing coating applied over at least a portion of the diamond-like glass coating, said fluorine-containing coating comprising an at least partially fluorinated compound.

Embodiment 80

A device or a component according to embodiment 79, wherein the at least partially fluorinated compound comprises at least one functional group which shares at least one covalent bond with the diamond-like glass coating.

Embodiment 81

A device or a component according to embodiment 80, wherein the fluorine-containing coating is covalently bonded to the diamond-like glass coating through a plurality of covalent bonds.

Embodiment 82

A device or a component according to embodiment 81, wherein the fluorine-containing coating is covalently bonded to the diamond-like glass coating through a plurality of covalent bonds including bonds in O—Si groups, in particular bonds in Si—O—Si groups

Embodiment 83

A device or a component according to any one of embodiments 80 to 82, wherein the at least one functional group of the at least partially fluorinated compound is a silane group.

Embodiment 84

A device or a component according to any one of embodiments 79 to 83, wherein the at least partially fluorinated compound comprises a polyfluoropolyether segment, in particular a perfluorinated polyfluoropolyether segment.

Embodiment 85

A device or a component according to any one of embodiments 79 to 84, wherein the at least partially fluorinated compound comprises a perfluorinated polyfluoropolyether segment, where in the repeating units of the perfluorinated polyfluoropolyether segment the number of carbon atoms in sequence is at most 6, in particular at most 4, more particularly at most 3 and most particularly at most 2.

Embodiment 86

A device or a component according to any one of embodiments 80 to 85, wherein the at least partially fluorinated compound comprising at least one functional group is a polyfluoropolyether silane, in particular a multifunctional polyfluoropolyether silane, and more particularly a difunctional polyfluoropolyether silane.

Embodiment 87

A device or a component according to embodiment 86, wherein the polyfluoropolyether segment(s) is (are) not linked to the silane group(s) via a functionality that includes a nitrogen-silicon bond or a sulfur-silicon bond.

Embodiment 88

A device or a component according to embodiment 86 or embodiment 87, wherein the polyfluoropolyether segment(s) is (are) linked to the silane group(s) via a functionality that includes a carbon-silicon bond, in particular via a —C(R)$_2$—Si functionality where R is independently hydrogen or a C$_{1-4}$ alkyl group, more particularly via a —(CR$_2$)$_k$—C(R)$_2$—Si functionality where k is at least 2 and where R is independently hydrogen or a C$_{1-4}$ alkyl group.

Embodiment 89

A device or a component according to embodiment 86or embodiment 87, wherein the fluorine-containing coating is a polyfluoropolyether-containing coating comprising polyfluoropolyether silane entities of the following Formula Ib:

$$R_f[Q\text{-}[C(R)_2\text{—}Si(O\text{—})_{3-x}(R^{1a})_x]_y]_z \quad \text{Ib}$$

which shares at least one covalent bond with the non-metal coating; and
wherein:
  $R_f$ is a monovalent or multivalent polyfluoropolyether segment;
  Q is an organic divalent or trivalent linking group;
  each R is independently hydrogen or a C$_{1-4}$ alkyl group;
  each Y is independently a hydrolyzable group;
  $R^{1a}$ is a C$_{1-8}$ alkyl or phenyl group;
  x is 0 or 1 or 2;
  y is 1 or 2; and
  z is 1, 2, 3, or 4.

Embodiment 90

A device or a component according to embodiment 89, wherein the at least one covalent bond shared with the non-metal coating is a bond to an oxygen atom in Si(O—)$_{3-x}$.

Embodiment 91

A device or a component according to embodiment 89or embodiment 90, wherein the polyfluoropolyether segment, $R_f$, comprises perfluorinated repeating units selected from the group consisting of —(C$_n$F$_{2n}$O)—, —(CF(Z)O)—, —(CF(Z)C$_n$F$_{2n}$O)—, —(C$_n$F$_{2n}$CF(Z)O)—, —(CF$_2$CF(Z)O)—, and combinations thereof; wherein n is an integer from 1 to 6 and Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted and wherein for repeating units including Z the number of carbon atoms in sequence is at most 6.

Embodiment 92

A device or a component according to embodiment 91, wherein n is an integer from 1 to 4 and wherein for repeating units including Z the number of carbon atoms in sequence is at most four.

Embodiment 93

A device or a component according to embodiment 92, wherein n is an integer from 1 to 3 and wherein for repeating units including Z the number of carbon atoms in sequence is at most three, more particularly the polyfluoropolyether segment, $R_f$, comprises perfluorinated repeating units selected from the group consisting of —(C$_n$F$_{2n}$O)—, —(CF(Z)O)—, and combinations thereof; wherein n is 1 or 2 and Z is an —CF$_3$ group.

Embodiment 94

A device or a component according to any one of embodiments 89 to 92, wherein z is 1 and $R_f$ is selected from the group consisting of C$_3$F$_7$O(CF(CF$_3$)CF$_2$O)$_p$CF(CF$_3$)—, CF$_3$O(C$_2$F$_4$O)$_p$CF$_2$—, C$_3$F$_7$O(CF(CF$_3$)CF$_2$O)$_p$CF$_2$CF$_2$—, C$_3$F$_7$O(CF$_2$CF$_2$CF$_2$O)$_p$CF$_2$CF$_2$—, C$_3$F$_7$O(CF$_2$CF$_2$CF$_2$O)$_p$CF(CF$_3$)— and CF$_3$O(CF$_2$CF(CF$_3$)O)$_p$(CF$_2$O)X—, wherein X is CF$_2$—, C$_2$F$_4$—, C$_3$F$_6$—, or C$_4$F$_8$— and wherein the average value of p is 3 to 50.

Embodiment 95

A device or a component according to any one of embodiments 89 to 92, wherein z is 2, and $R_f$ is selected from the group consisting of —CF$_2$O(CF$_2$O)$_m$(C$_2$F$_4$O)$_p$CF$_2$—, —CF(CF$_3$)O(CF(CF$_3$)CF$_2$O)$_p$CF(CF$_3$)—-CF(CF$_3$)—(OCF$_2$CF(CF$_3$))$_p$O—C$_t$F$_{2t}$—O(CF(CF$_3$)CF$_2$O)$_p$CF(CF$_3$)—, —CF$_2$O(C$_2$F$_4$O)$_p$CF$_2$—, —(CF$_2$)$_3$O(C$_4$F$_8$O)$_p$(CF$_2$)$_3$—, wherein t is 2, 3 or 4 and wherein m is 1 to 50, and p is 3 to 40.

Embodiment 96

A device or a component according to embodiment 95, wherein $R_f$ is selected from the group consisting of —CF$_2$O(CF$_2$O)$_m$(C$_2$F$_4$O)$_p$CF$_2$—, —CF$_2$O(C$_2$F$_4$O)$_p$CF$_2$—, and —CF(CF$_3$)—(OCF$_2$CF(CF$_3$))$_p$O—(C$_t$F$_{2t}$)—O(CF(CF$_3$)CF$_2$O)$_p$CF(CF$_3$)—, and wherein t is 2, 3 or 4, and wherein the average value of m+p or p+p or p is from about 4 to about 24.

Embodiment 97

A device or a component according to any one of embodiments 89 to 96, wherein Q is selected from the group consisting of —C(O)N(R)—(CH$_2$)$_k$—, —S(O)$_2$N(R)—(CH$_2$)$_k$—, —(CH$_2$)$_k$—, —CH$_2$O—(CH$_2$)$_k$—, —C(O)S—(CH$_2$)$_k$—, —CH$_2$OC(O)N(R)—(CH$_2$)$_k$—, and

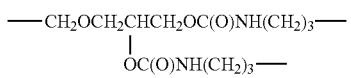

wherein R is hydrogen or $C_{1-4}$ alkyl, and k is 2 to about 25.

Embodiment 98

A device or a component according to embodiment 97, wherein Q is selected from the group consisting of —C(O)N(R)(CH$_2$)$_2$—, —OC(O)N(R)(CH$_2$)$_2$—, —CH$_2$—O—(CH$_2$)$_2$—, or —CH$_2$—OC(O)N(R)—(CH$_2$)$_2$—, wherein R is hydrogen or $C_{1-4}$ alkyl and y is 1.

Embodiment 99

A device or a component according to any one of embodiments 88 to 98, wherein R is hydrogen; and/or wherein x is 0.

Embodiment 100

A device or a component according to any one of embodiments 89 to 93 or any one of 95 to 99, wherein $R_f$ is —CF$_2$O(CF$_2$O)$_m$(C$_2$F$_4$O)$_p$CF$_2$—, and Q-C(R)$_2$—Si(O—)$_{3-x}$(R$^{1a}$)$_x$ is C(O)NH(CH$_2$)$_3$Si(O—)$_3$ and wherein m is 1 to 50 and p is 3 to 40, in particular wherein the average value of m+p or p is from about 4 to about 24, more particularly wherein m and p are each about 9 to about 12.

Embodiment 101

A device or a component according to any one of embodiments 89 to 94 or any one of claims 96 to 99, wherein $R_f$ is C$_3$F$_7$O(CF(CF$_3$)CF$_2$O)$_p$CF(CF$_3$)—, and Q-C(R)$_2$—Si(O—)$_{3-x}$(R$^{1a}$)$_x$ is C(O)NH(CH$_2$)$_3$Si(O—)$_3$, wherein p is 3 to 50, in particular wherein p is from about 3 to about 20, more particularly p is from about 4 to about 10.

Embodiment 102

A device or a component according to any one of embodiments 84 to 101, wherein the weight average molecular weight of the polyfluoropolyether segment is about 900 or higher, in particular 1000 or higher; and/or the weight average molecular weight of the polyfluoropolyether segment is about 6000 or less, in particular about 4000 or less, more particularly about 3000 or less.

Embodiment 103

A device or a component according to any one of embodiments 86 to 102, wherein the amount of polyfluoropolyether silane having a polyfluoropolyether segment having a weight average molecular weight less than 750 is not more than 10% by weight of total amount of polyfluoropolyether silane, in particular not more than 5% by weight of total amount of polyfluoropolyether silane, more particularly not more than 1% by weight of total amount of polyfluoropolyether silane, and most particular 0% by weight of total amount of polyfluoropolyether silane.

Embodiment 104

A device or a component according to any one of embodiments 89 to 103, wherein the fluorine-containing coating comprises at least the following two polyfluoropolyether silane entities in accordance with Formula Ib:

(a) a first polyfluoropolyether silane entity where $R_f$ is C$_3$F$_7$O(CF(CF$_3$)CF$_2$O)$_p$CF(CF$_3$)—, and Q-C(R)$_2$—Si(O—)$_{3-x}$(R$^{1a}$)$_x$ is C(O)NH(CH$_2$)$_3$Si(O—)$_3$, wherein p is 3 to 50, in particular wherein p is from about 3 to about 20, more particularly p is from about 4 to about 10; and (b) a second polyfluoropolyether silane entity where $R_f$ is —CF$_2$O(CF$_2$O)$_m$(C$_2$F$_4$O)$_p$CF$_2$—, and Q-C(R)$_2$—Si(O—)$_{3-x}$(R$^{1a}$)$_x$ is C(O)NH(CH$_2$)$_3$Si(O—)$_3$ and wherein m is 1 to 50 and p is 3 to 40, in particular wherein the average value of m+p or p is from about 4 to about 24, more particularly wherein m and p are each about 9 to about 12

Embodiment 105

A device or a component according to embodiment 104, wherein the weight percent ratio of the first to second polyfluoropolyether silane entity (first polyfluoropolyether silane entity:second fluoropolyether silane entity) is equal to or greater than 10:90, in particular equal to or greater than 20:80, more particularly equal to or greater than 30:70, most particularly equal to or greater than 40:60; and/or wherein the weight percent ratio of the first to second polyfluoropolyether silane (first polyfluoropolyether silane:second polyfluoropolyether silane) is equal to or less than 99:1, in particular equal to or less than 97:3, most particularly equal to or less than 95:5.

Embodiment 106

A device or a component to any one of embodiments 79 to 105, wherein the fluorine-containing coating has a thickness greater tan 15 Angstroms, in particular at least about 2 nm, more particularly at least about 10 nm, even more particularly at least about 25 nm, and most preferably at least about 40 nm; and/or wherein the fluorine-containing coating has a thickness of at most about 200 nm, in particular at most about 150 nm, more particularly at most about 100 nm.

Embodiment 107

A device or a component according to any one of embodiments 65 to 78, wherein the device or component, respectively, is free of a fluorine-containing over-coating on said diamond-like glass coating, in particular free of an overcoating on said diamond-like glass coating.

Embodiment 108

A device or a component according to any one of embodiments 65 to 107, where said surface of the device or said surface of the component of the device, as applicable, is a surface that is or will come in contact with a medicament or a medicinal formulation during storage or delivery from the medicinal inhalation device.

Embodiment 109

A device or a component according to any one of embodiments 65 to 108, wherein said surface of the device or said surface of the component of the device, as applicable, is a surface that comes in contact with a movable component of the device or is a surface of a movable component of the device.

Embodiment 110

A device or a component according to any one of embodiments 65 to 109, where said medicinal inhalation device is a metered dose inhaler or a dry powder inhaler.

Embodiment 111

A component according to embodiment 64 or any one of embodiments 65 to 110, wherein the component is a component of a metered dose inhaler and the component is selected from the group consisting of an actuator, an aerosol container, a ferrule, a valve body, a valve stem and a compression spring, in particular an aerosol container.

Embodiment 112

A component according to embodiment 64 or any one of embodiments 65 to 110, wherein the component is a component of a dry powder inhaler and the component is selected from the group consisting of a powder container, powder carrier, a component used to open a sealed powder container, a component that defines at least in part a deagglomeration chamber, a component of a deagglomeration system, a component that defines at least in part a flow channel, a dose-transporting component, a component that defines at least in part a mixing chamber, a component that defines at least in part an actuation chamber, a mouthpiece and a nosepiece.

Embodiment 113

A component according to embodiment 64 or any one of embodiments 65 to 110, wherein the component is a component of a breath-actuating device or a component of a breath-coordinating device or a spacer or a component of a spacer or a component of a dose counter for a medicinal inhalation device.

Embodiment 114

A device according to embodiment 64 or any one of embodiments 65 to 110, wherein the device is a metered dose inhaler and the inhaler contains a medicinal aerosol formulation comprising a medicament and HFA 134a and/or HFA 227.

Embodiment 115

A device according to embodiment 114, wherein said surface of the metered dose inhaler is at least the interior surface of the aerosol container, in particular an aerosol container made of aluminum, aluminum alloy, stainless steel, glass, or a polymer.

Embodiment 116

A device according to embodiment 114 or embodiment 115, wherein said surface of the metered dose inhaler is all interior surfaces that is or will come in contact with the medicinal aerosol formulation during storage or delivery from the metered dose inhaler.

Embodiment 117

A device according to any one of embodiments 114 to 116, wherein the medicinal aerosol formulation comprises a medicament that is dispersed in said formulation; and/or the medicinal aerosol formulation comprises a chloride and/or a bromide salt of a medicament; and/or the medicinal aerosol formulation comprises a corticosteroid, in particular a 20-ketosteroid, more particular a 20-ketosteroid including an —OH group at the C17 and/or C21 position.

Embodiment 118

A device according to any one of embodiments 114 to 117, wherein the medicinal aerosol formulation comprises a medicament that is dispersed in said formulation and wherein the medicinal aerosol formulation comprises at most 0.005 wt % with respect to the formulation of surfactant and/or less than 5 wt % with respect to the formulation of ethanol.

Embodiment 119

A device according to any one of embodiments 114 to 118, wherein the medicinal aerosol formulation is substantially free of surfactant, in particular free of surfactant, and/or wherein the medicinal aerosol formulation is substantially free, in particular free of ethanol.

Embodiment 120

A device according to any one of embodiments 114 to 119, wherein the medicinal aerosol formulation comprises a medicament selected from the group consisting of salbutamol, terbutaline, ipratropium, oxitropium, tiotropium, daratropium, aclidinium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, oglemilast, zileuton, insulin, pentamidine, calcitonin, leuprolide, alpha-1-antitrypsin, interferon, triamcinolone, and pharmaceutically acceptable salts and esters thereof and mixtures thereof The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

BRIEF DESCRIPTION OF DRAWINGS

The invention will now be described with reference to the accompanying drawings in which.

DETAILED DESCRIPTION

It is to be understood that the present invention covers all combinations of particular, suitable, desirable, favorable, advantageous and preferred aspects of the invention described herein.

Figure 1A:
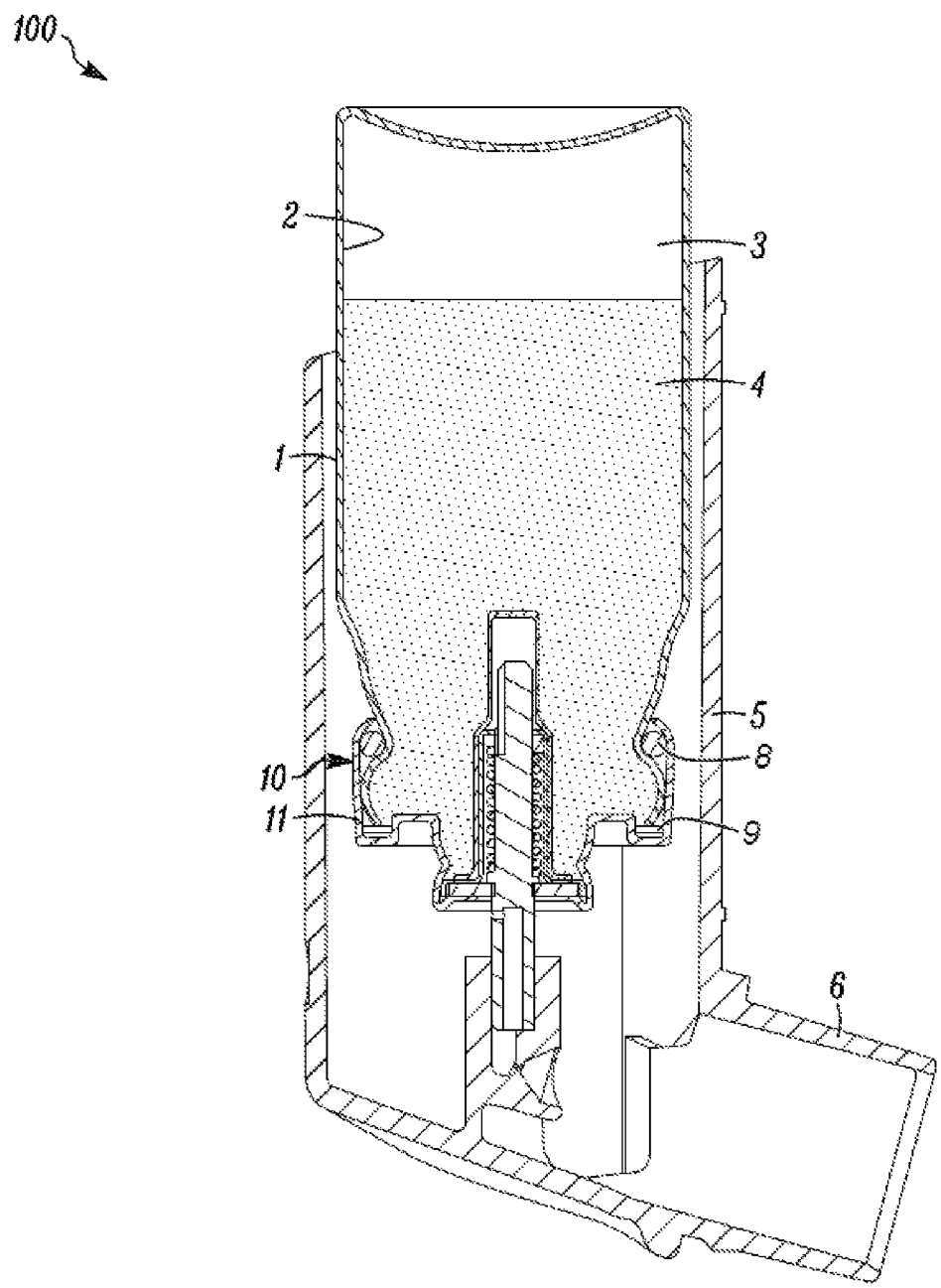
FIG. 1a represents a schematic cross-sectional view of a pressurized metered dose inhaler known in the art and FIG. 1b represents an enlarged view of a portion of the inhaler.

For better understanding of the present invention, in the following an exemplary, well known pressurized metered dose inhaler (FIG. 1) will be first described. In particular, FIG. 1a shows a metered dose dispenser (100), in particular an inhaler, including an aerosol container (1) fitted with a metered dose valve (10) (shown in its resting position).

Aerosol containers for metered dose inhalers are typically made of aluminum or an aluminum alloy. Aerosol containers may be made of other materials, such as stainless steel, glass, plastic (e.g., polyethylene terephthalate, polycarbonate, polyethylene, high density polyethylene and polypropylene) and ceramics.

Returning to FIG. 1a, the valve is typically affixed, i.e., crimped, onto the container via a cap or ferrule (11) (typically made of aluminum or an aluminum alloy) which is generally provided as part of the valve assembly. Between the container and the ferrule there may be one or more seals. In the embodiments shown in FIGS. 1a and 1b between the container (1) and the ferrule (11) there are two seals including e.g., an O-ring seal (8) and the gasket seal (9). The illustrated valve is a commercial valve marketed under the trade designation SPRAYMISER by 3M Company, St. Paul, Minn., USA. As shown in FIG. 1a, the container/valve dispenser is typically provided with an actuator (5) including an appropriate patient port (6), such as a mouthpiece. For administration to the nasal cavities the patient port is generally provided in an appropriate form (e.g., smaller diameter tube, often sloping upwardly) for delivery through the nose. Actuators are generally made of a plastic, for example polypropylene or polyethylene. As can be seen from FIG. 1a, the inner walls (2) of the container and the outer walls of the portion(s) of the metered dose valve located within the container defined a formulation chamber (3) in which aerosol formulation (4) is contained.

Depending on the particular metered dose valve and/or filling system, aerosol formulation may be filled into the container either by cold-filling (in which chilled formulation (chilled to temperatures of about −50 to −55° C. for propellant HFA 134a-based formulations) is filled into the container and subsequently the metered dose valve is crimped onto the container) or by pressure filling (in which the metered dose valve is crimped onto the container and then formulation is pressure filled through the valve into the container).

After filling of the aerosol formulation and crimping on the valve, regardless of the order, typically the container/valve device is tested for leaks by immersing the device in a water bath for 3 minutes at 55° C.

An aerosol formulation used in a metered dose inhaler typically comprises a medicament or a combination of medicaments and liquefied propellant selected from the group consisting of HFA 134a, HFA 227 and mixtures thereof. Aerosol formulations may, as desired or needed, comprise other excipients, such as surfactant, a co-solvent (e.g., ethanol), $CO_2$, or a particulate bulking agent. Medicament may be provided in particulate form (generally having a median size in the range of 1 to 10 microns) suspended (i.e., dispersed) in the liquefied propellant. Alternatively medicament may be in solution (i.e., dissolved) in the formulation. In the event a combination of two or more medicaments is included, all the medicaments may be suspended or in solution or alternatively one or more medicaments may be suspended, while one or more medicaments may be in solution. A medicament may be a drug, vaccine, DNA fragment, hormone or other treatment. The amount of medicament would be determined by the required dose per puff and available valve sizes, which are typically 25, 50 or 63 microliters, but may include 100 microliters where particularly large doses are required. Suitable drugs include those for the treatment of respiratory disorders, e.g., bronchodilators, anti-inflammatories (e.g., corticosteroids), anti-allergics, anti-asthmatics, anti-histamines, and anti-cholinergic agents. Therapeutic proteins and peptides may also be employed for delivery by inhalation. Exemplary drugs which may be employed for delivery by inhalation include but are not limited to: salbutamol, terbutaline, ipratropium, oxitropium, tiotropium, daratropium, aclidinium, beclomethasone, flunisolide, budesonide, mometasone, ciclesonide, cromolyn sodium, nedocromil sodium, ketotifen, azelastine, ergotamine, cyclosporine, salmeterol, fluticasone, formoterol, procaterol, indacaterol, TA2005, omalizumab, oglemilast, zileuton, insulin, pentamidine, calcitonin, leuprolide, alpha-1-antitrypsin, interferons, triamcinolone, and pharmaceutically acceptable salts and esters thereof such as salbutamol sulfate, formoterol fumarate, salmeterol xinafoate, beclomethasone dipropionate, triamcinolone acetonide, fluticasone propionate, fluticasone furoate, tiotropium bromide, leuprolide acetate and mometasone furoate.

Pressurized metered dose inhalers including e.g., metal aerosol containers whose interior surfaces are coated in accordance with certain aspects described herein are particularly advantageous for containing and delivering corticosteroids, particularly 20-ketosteroids, including those with an —OH group at the C17 and/or C21 position, such as budesonide, which may undergo degradation when in contact with metal oxides, as well as other medicaments, such as salbutamol, formoterol, salmeterol, TA2005 and salts thereof, which are susceptible to degradation when in contact with common container materials, such as aluminum.

Pressurized metered dose inhalers including e.g., metal aerosol containers (and metal valve components) whose interior surfaces are coated in accordance with certain aspects described herein are particularly advantageous for containing and delivering solution formulations containing chloride or bromide salts of medicaments, such as ipratropium bromide, oxitropium bromide, tiotropium bromide or pirbuterol hydrochloride, the presence of such electrolyte formulations in combination with for example uncoated aluminum containers and stainless steel valve components may cause an undesired formation of a galvanic cell.

Pressurized metered dose inhalers including e.g., aerosol containers (in particular metal aerosol containers) whose interior surfaces are coated in accordance with certain aspects described herein are particularly advantageous for containing and delivering medicinal aerosol formulations comprising a medicament that is dispersed in said formulation.

In addition, embodiments described in detail below, in accordance with the present invention are particularly useful in regard to pressurized metered dose inhalers including a medicinal aerosol formulation that includes low amounts of surfactant (at most 0.005 wt % with respect to the formulation); or is substantially free (less than 0.0001 wt % with respect to drug) or free of a surfactant. Alternatively or additionally, embodiments described in detail below, are particularly useful in metered dose inhalers including a medicinal aerosol formulation that contains low amounts of ethanol (less than 5 wt % with respect to the formulation), or is substantially free (less than 0.1 wt % with respect to the formulation) or free of ethanol.

Figure 1B:
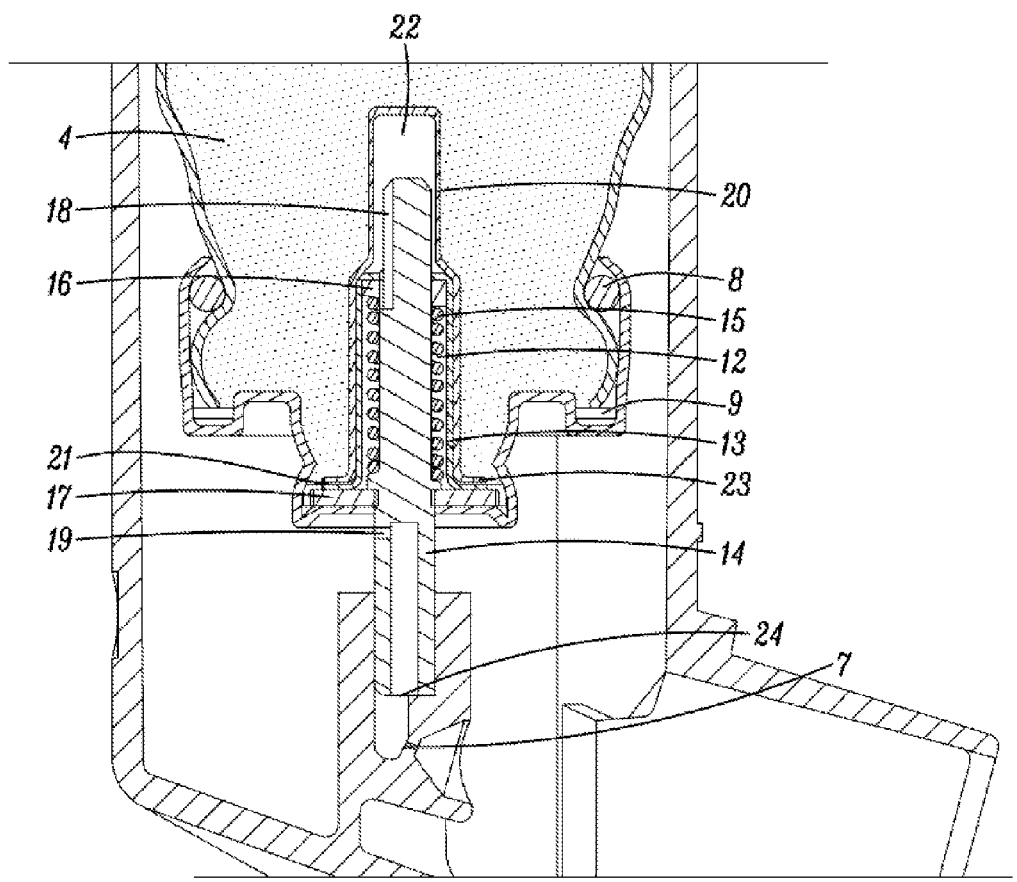

The valve shown in FIG. 1a, better viewed in FIG. 1b, includes a metering chamber (12), defined in part by an inner valve body (13), through which a valve stem (14) passes. The valve stem, which is biased outwardly by a compression spring (15), is in sliding sealing engagement with an inner tank seal (16) and an outer diaphragm seal (17). The valve also includes a second valve body (20) in the form of a bottle emptier. The inner valve body (referred to in the following as the "primary" valve body) defines in part the metering chamber. The second valve body (referred to in the following as the "secondary" valve body) defines in part a pre-metering region or chamber besides serving as a bottle emptier.

Referring to FIG. 1b, aerosol formulation (4) can pass from the formulation chamber into a pre-metering chamber (22)

provided between the secondary valve body (20) and the primary valve body (13) through an annular space (21) between the flange (23) of the secondary valve body and the primary valve body. To actuate (fire) the valve, the valve stem (14) is pushed inwardly relative to the container from its resting position shown in FIGS. 1a and b, allowing formulation to pass from the metering chamber through a side hole (19) in the valve stem and through a stem outlet (24) to an actuator nozzle (7) then out to the patient. When the valve stem (14) is released, formulation enters into the valve, in particular into the pre-metering chamber (22), through the annular space (21) and thence from the pre-metering chamber through a groove (18) in the valve stem past the tank seal (16) into the metering chamber (12).

With the exception of the elastomeric seals used in metered dose valves, typically the components of such valves are made of metal (e.g., stainless steel, aluminum or aluminum alloy) or plastic. For example compression springs are generally made of a metal, in particular stainless steel as the conventional material. Compression springs may also be made of aluminum or aluminum alloy. Valve stems and valve bodies are generally made of metal and/or plastic; as a metal conventionally stainless steel is used (other metals that may be used include aluminum, aluminum alloy and titanium) and as plastics conventionally polybutylene terephthalate (PBT) and/or acetal are used (other polymers that may be used include polyetheretherketones, nylon, other polyesters (such as tetrabutylene terephthalate), polycarbonates and polyethylene).

Favorably at least a portion of a surface, more favorably the entire surface, of a component or components of a medicinal inhalation device (e.g., aerosol containers, actuators, ferrules, valve bodies, valve stems or compression springs of metered dose inhalers or powder containers or carriers of dry powder inhalers) which is or will come in contact with a medicament or a medicinal formulation during storage or delivery from the medicinal inhalation device are treated according to methods described herein. The entire surface of the component, including any surface or surfaces (if present) that do not or will not come in contact with a medicament or a medicinal formulation during storage or delivery from the device, may also be treated according to methods described herein. For example, a compartment in a dry powder inhaler may be coated to reduce moisture permeation into it, in order to protect drug contained therein. Alternatively or additionally, favorably at least a portion of a surface, more favorably the entire surface, of a component or components of a medicinal inhalation device, which either come in contact with a movable component and/or are movable during storage or delivery from the medicinal inhalation device are treated according to methods described herein. Examples of such components for pressurized metered dose inhalers include e.g., aerosol containers, valve bodies, valve stems or compression springs of metered dose valves.

In particular a component of a medicinal inhalation device in accordance with the present invention or made according to methods in accordance with the present invention is a component of a metered dose inhaler. Said component may be selected from the group consisting of aerosol container, an actuator, a ferrule, a valve body (e.g., a primary and/or a secondary valve body), a valve stem and a compression spring. Alternatively a component of a medicinal inhalation device in accordance with the present invention or made according to methods in accordance with the present invention is a component of a dry powder inhaler. Said component may be selected from the group consisting of a component that defines at least in part a powder container or carrier (e.g., a multidose reservoir container or single dose blister or capsule or tape), a component used to open a sealed powder container (e.g., piercer to open single dose blisters or capsules), a component that defines at least in part a deagglomeration chamber, a component of a deagglomeration system, a component that defines at least in part a flow channel, a dose-transporting component (e.g., a dosing rod, dosing wheel or dosing cylinder with a recess dimensioned to accommodate a single dose of powder trapped between said component and a housing in which it moves to transport the dose), a component that defines at least in part a mixing chamber, a component that defines at least in part an actuation chamber (e.g., a holding chamber where a dose is dispensed prior to inhalation), a mouthpiece and a nosepiece. Diamond-like-glass coatings as described herein may be favorably applied to a surface or surfaces along the flow path of drug in order to advantageously minimize residual drug adhering to such surfaces, in order to reduce drug loss resulting in inaccurate dosing, or to allow components to move relative to one another unimpeded by powder.

Embodiments in accordance with certain aspects of the present invention include forming by plasma deposition under ion bombardment conditions a non-metal coating on at least a portion of a surface of a medicinal inhalation device or a component of a medicinal inhalation device (e.g., an aerosol container of a metered dose inhaler, a metered dose valve or a component thereof, or a powder container or carrier of a dry powder inhaler), where the formed non-metal coating is a diamond-like glass comprising hydrogen and on a hydrogen free basis from about 20 to about 40 atomic percent of silicon, equal to or greater than 39 atomic percent of carbon, and less than 33 down to and including zero atomic percent of oxygen.

Embodiments in accordance with other aspects of the present invention include a medicinal inhalation device or a component of a medicinal inhalation device comprising a diamond-like glass coating on at least a portion of a surface of the device or component, respectively, where the diamond-like glass coating comprising hydrogen and on a hydrogen free basis from about 20 to about 40 atomic percent of silicon, equal to or greater than 39 atomic percent of carbon, and less than 33 down to and including zero atomic percent of oxygen. Favorably said coating is plasma deposited under ion bombardment conditions.

Such diamond-like glass coatings are advantageously covalently bonded to the at least a portion of the surface of the device or the component, respectively.

Here plasma deposition (which may be suitably microwave, inductively coupled, DC, AC or RF (radio frequency) plasma deposition, more suitably microwave, inductively coupled or RF plasma deposition, most suitably RF plasma deposition) is carried out in such a way that an ion sheath is formed upon generation of the plasma (plasma formed from an appropriate source compound or compounds, typically an organosilicon as discussed in more detail below) and where the substrate, whose surface is or surfaces are to be coated, is positioned within the plasma system so that during plasma deposition the substrate is within the ion sheath. An explanation of the formation of ion sheaths can be found in Brian Chapman, Glow Discharge Processes, 153 (John Wily & Sons, New York 1980). For RF-plasma deposition, this can be generally accomplished through the use of a RF-powered electrode and locating the substrate to be coated in proximity to the RF-powered electrode. For microwave plasma deposition and inductively coupled plasma deposition, this can be accomplished by providing the microwave or inductively coupled plasma system, respectively, with an electrode, biasing (generally negatively biasing) this electrode and locating the substrate in proximity to said biased electrode. For DC plasma deposition, this can be accomplished by locating the substrate in proximity to the cathode or negatively biased electrode (e.g., for providing thin coatings of 10 nm or less). In this manner plasma deposition occurs under conditions of ion bombardment. In particular, polymerized species formed in the plasma are subjected to ion bombardment, and are thus among other things fragmented, before depositing and/or upon deposition on the substrate allowing the provision of an advantageous, dense, random, covalent system on the surface(s) of the substrate. Moreover because the substrate, whose surface is or surfaces are to be coated, is located within an ion sheath, ions accelerating toward the electrode bombard the species being deposited from the plasma onto the substrate and thus the substrate is exposed to the ion bombarded species being deposited from the plasma. The resulting reactive species within the plasma react on the surface of the substrate, forming a coating, the composition of which is controlled by the composition of the gas being ionized in the plasma. The species forming the coating are advantageously attached to the surface of the substrate by covalent bonds, and therefore the coating is advantageously covalently bonded to the substrate. Such amorphous covalent systems show excellent adhesion (through e.g., covalent bonding) to many substrate materials, including metals, polymers, glass and ceramics. Such covalent amorphous systems provide "sharp" coatings e.g., on complex-formed components such as valve stems or compression springs. Such covalent amorphous systems are desirable in that they are typically transparent or translucent. Furthermore, such amorphous covalent systems show advantageously high atomic packing densities, typically in a range from about 0.20 to about 0.28 (in particular from about 0.22 to about 0.26) gram atom number density in units of gram atoms per cubic centimeter. Polymeric coatings (e.g., plasma polymer coatings) generally have gram atom number densities around 0.18. Such high atomic packing densities allow the provision of coatings having a minimum of porosity, excellent resistance to diffusion to liquid or gaseous materials, and superb, "diamond-like" hardness. Microhardness of diamond-like glass coatings described herein, as determined using a nanoindenter, are generally, favorably at least 1 GPa, more favorably at least 2 GPa. Such coatings may also have desirable surface characteristics, including e.g., poor wettability and low surface energy.

As mentioned above, oxygen-lean to oxygen free diamond-like glass coatings described herein have been found to have superior structural integrity, first having desirable durability over the lifetime of medicinal inhalation device and secondly having desirable robustness advantageous for particular manufacturing operations. In particular, again as mentioned above, such diamond-like glass coatings show desirable expansion/stretching capabilities with marked flexibility, such properties being generally, continually further enhanced as the oxygen content approaches zero. Microelastic-modulus of such coatings, as determined using a nanoindenter, is generally, favorably less than 11 GPa.

Oxygen-lean to oxygen-free diamond-like glass coatings include hydrogen and on a hydrogen free basis about 20 to about 40 atomic percent of silicon, greater than 39 atomic percent of carbon, and less than 33 down to and including zero atomic percent of oxygen. Favorably such diamond-like glass coatings contain on a hydrogen free basis from about 20 to about 40 atomic percent of silicon, greater than 42 atomic percent of carbon, less than 30 down to and including zero atomic percent of oxygen; more favorably from about 20 to about 40 atomic percent of silicon, greater than 45 atomic percent of carbon, less than 28 down to and including zero atomic percent of oxygen; even more favorably from about 20 to about 40 atomic percent of silicon, greater than 50 atomic percent of carbon, less than 25 down to and including zero atomic percent of oxygen; yet even more favorably from about 20 to about 40 atomic percent of silicon, greater than 50 atomic percent of carbon, less than 20 down to and including zero atomic percent of oxygen, and yet even further more favorably from about 20 to, but not including 40 atomic percent of silicon, greater than 60 atomic percent of carbon, less than 15 down to and including zero atomic percent of oxygen. Desirably in such diamond-like glass coatings, the content of oxygen (on a hydrogen-free basis) is zero up to and including about 12 atomic percent. Favorably in such diamond-like glass coatings the content of silicon (on a hydrogen-free basis) is in the range from about 20 to about 35 atomic percent. "Hydrogen free basis" refers to the atomic composition of a material (i.e., in atomic percent) as established by a method such as X-ray photoelectron spectroscopy (XPS) which does not detect hydrogen even if large amounts are present in the coating. Again the combination of a fairly high amount of silicon with significant amounts of carbon (in each case higher than that of oxygen) and amounts of oxygen less than 33% going down to zero surprisingly makes diamond-like glass coatings especially expandable together with favorable flexibility (unlike glass or amorphous carbon coatings such as diamond-like carbon coatings). Diamond-like glass coatings described herein have relatively low intrinsic stress and thus excellent long-term adhesion and durability (unlike diamond-like carbon coatings which have a tendency to flake off due to relatively high intrinsic stress within the coating). Thus diamond-like glass coatings described herein are particularly advantageous as coatings on a surface or surfaces of a medicinal inhalation device component which undergoes movement in itself (e.g., a compression spring of a metered dose valve) or movement in conjunction with or relative to other components (e.g., a valve stem of a metered dose valve). Diamond-like glass coatings as well as methods of making diamond-like glass and apparatus for depositing diamond-like glass are described in U.S. Pat. No. 6,696,157 (David et al) the content of which is incorporated here in its entirety.

It is to be recognized that plasma deposition under conditions of ion bombardment is distinct from plasma polymerization. In plasma polymerization, polymerized species formed in the plasma deposit (as is) on the substrate to provide a polymer coating on the surface(s) of the substrate. Moreover in plasma polymerization techniques, plasma deposition is carried out in such a manner that no ion sheath is formed (e.g., using conventional microwave or inductively coupled plasma systems) or the substrate to be coated with the polymer is positioned outside of any ion sheath, if at all formed. For example, in regard to the RF-plasma systems using a RF-powered electrode, for plasma polymerization, i.e., deposition of the polymer on the substrate, the substrate is located in proximity to the grounded electrode or placed at a floating potential (i.e., electrically isolated and located outside of any ion sheath formed during RF-plasma deposition).

The term "plasma deposition" as used herein, unless otherwise specified, will be understood to be plasma deposition under conditions of ion bombardment. Similarly the term "plasma deposited" as used herein, unless otherwise specified, will be understood to be plasma deposited under ion bombardment.

Forming a diamond-like glass coating as described herein by plasma deposition can be carried out in a suitable reaction chamber having a capacitively-coupled system with at least one electrode powered by an RF (radio frequency) source and at least one grounded electrode, such as those described in U.S. Pat. No. 6,696,157 (David et al.) and U.S. Pat. No. 6,878,419 (David et al.). Other apparatuses include those schematically illustrated and described in the co-pending application PCT/US2008/082600. For the plasma deposition under conditions of ion bombardment, an apparatus described in PCT/US2008/082600 may include a grounded chamber (also acting here as a grounded electrode) from which air is removed by a pumping stack, where gas or gases to form the plasma are generally injected radially inwardly through the reactor wall to an exit pumping port in the center of the chamber. A substrate to be coated (typically a medicinal inhalation device component per se or alternatively a workpiece from which such a component may be subsequently formed or worked) would be positioned proximate the RF-powered electrode (insulated from the chamber) so that the substrate will be located within the ion sheath. Another exemplary apparatus is described in PCT/US2008/082600 for the plasma deposition under conditions of ion bombardment, where a substrate or a plurality of substrates (again such substrate(s) being typically medicinal inhalation device component(s) per se or alternatively a work-piece(s) from which such a component may be subsequently formed or worked) are tumbled during deposition, such tumbling favorably allowing for uniform deposition on the surfaces of the substrate(s). Here the chamber is a tube, in particular a quartz tube, the ends of which are sealed with e.g., aluminum flanges, each flange typically provided with a port, one port being connected to a pumping stack and the other being connected to a gas supply system. The ports together with the connecting-system are favorably configured and arranged to allow for rotation of the tube and thus the chamber during plasma deposition. The RF-powdered electrode is configured as an arc conforming to the curvature of the tube and is positioned just underneath the tube but separated from the tube by a narrow gap. During treatment with such a system, the chamber is rotated so the substrate(s) to be coated tumble; tumbling can be desirably facilitated through the inclusion of baffles within the tube. Through an appropriate degree of substrate loading together with tumbling at an appropriate rate during plasma deposition, the substrate(s) to be coated will be found within the lower portion of the tube, and thus positioned in proximity of the RF-powered electrode so that the substrate(s) will be located within the ion sheath. An additional system is described below in conjunction with the Examples.

Before plasma deposition, it is desirable to expose the substrate to an oxygen plasma or alternatively an argon plasma, more desirably an oxygen plasma. It is most desirable to expose the substrate to an oxygen plasma under conditions of ion bombardment (i.e., generating an ion sheath and having the substrate located within the ion sheath during said oxygen plasma treatment). Typically for this pre-treatment, power densities in the range from about 0.10 to about 0.95 watts/square cm can be applied. Also generally for this pre-treatment, flow densities (of the pre-treating gas, e.g., oxygen or argon) in the range from about 0.01 to about 1 sccm/square cm, preferably about 0.05 to 1 about sccm/square cm, most preferably, about 0.1 to about 0.6 sccm/square cm can be applied.

Power density is a ratio of the plasma power (typically in watts) and the surface area (typically in square cm) of the substrate to-be-coated (i.e., the density of plasma power at or upon the surface to-be-coated). Similarly flow density is a ratio of the flow (typically in standard cubic centimeters per minute (sccm)) of the gas in question and the surface area of the substrate to-be coated.

A solvent washing step with an organic solvent such as acetone or ethanol may also be included prior to the exposure to an oxygen or argon plasma as described above. Also generally the plasma deposition system is evacuated to any extent necessary to remove air and any impurities.

For the provision of a plasma deposited diamond-like glass coating a gas comprising one or more organosilicon is introduced into the system at a desired and/or needed flow rate. Favorably the flow rates are selected so that a sufficient flow is provided to establish a suitable pressure at which to carry out plasma deposition. Favorably the pressure at the surface to-be-coated is greater than 100 millitorr, in particular equal to or greater than 300 millitorr, more particularly in the range from 500 millitorr to 5000 millitorr. Favorably the flow density of the organosilicon applied is greater than about 0.01 sccm/square cm, more favorably greater than about 0.05 sccm/square cm, most favorably greater than about 0.1 sccm/square cm. Favorably flow densities are less than about 0.30 sccm/square cm, more favorably less than about 0.25 sccm/square cm. Flow density of organosilicon refers to the organosilicon gas per se or if a mixture of organosilicon compounds is being used, the mixture of organosilicons (i.e., without any non-organosilicon assist gases, if used). It has been found that high pressures at the surface to-be-coated and/or high flow densities are advantageous in providing superior coating densities as well as uniform and conformal coatings having a high degree of flexibility and resistance to cracking, and thus further enhancing barrier properties of oxygen-lean/free diamond-like glass coatings described herein.

An RF electric field is applied to the powered electrode, ionizing the gas and establishing a plasma. Favorably the plasma density is greater than about 0.10 watts/square cm. It has been found advantageous in facilitating the provision of flexible coatings, to apply lower power density in combination with longer deposition times. In the RF-generated plasma, energy is coupled into the plasma through electrons. The plasma acts as the charge carrier between the electrodes. The plasma is typically visible as a colored cloud. The plasma also forms an ion sheath proximate at least to the RF-powered electrode. The ion sheath typically appears as a darker area around the electrode. The depth of the ion sheath normally ranges from about 1 mm to about 50 mm and depends on factors such as the type and concentration of gas used, pressure, the spacing between the electrodes, and relative size of the electrodes. For example, reduced pressures will increase the size of the ion sheath. When the electrodes are different sizes, a larger, stronger ion sheath will form around the smaller electrode. Generally, the larger the difference in electrode size, the larger the difference in the size of the ion sheaths, and increasing the voltage across the ion sheath will increase ion bombardment energy.

For favorable embodiments plasma deposition comprises ionizing a gas comprising at least one organosilicon compound. Typically the silicon of the at least one organosilicon compound is present in an amount of at least about 5 atomic percent of the gas mixture. In particular the organosilicon comprises at least one of trimethylsilane, triethylsilane, trimethoxysilane, triethoxysilane, tetramethylsilane, tetraethylsilane, tetramethoxysilane, tetraethoxysilane, hexamethylcyclotrisiloxane, tetramethylcyclotetrasiloxane, tetraethylcyclotetrasiloxane, octamethylcyclotetrasiloxane, hexamethyldisiloxane, and bistrimethylsilylmethane. Tetramethylsilane and tetraethyoxysilane have been found to be particularly useful, more particularly tetramethylsilane.

The gas comprising an organosilicon (referred to in the following as the source gas) may further comprise an additional gas or gases. Each additional gas can be added separately or in combination with each other. If a gas is mixed along with the organosilicon compound(s), the atomic percent of silicon in the gas mixture generally is calculated based on the volumetric (or molar) flow rates of the component gases in the mixture. The source gas may for example further comprise argon and/or hydrogen, in particular for plasma deposition under ion bombardment conditions. The application of argon (normally is not incorporated into the deposited coating) enhances ion bombardment, while the application of hydrogen promotes the formation of high packing density as well as provides an additional source of hydrogen. Optionally the source gas may further comprise ammonia and/or nitrogen. However for certain preferred embodiments, described in more detail infra, in which a composition comprising an at least partially fluorinated compound comprising at least one silane group will be applied, it is desirable not to use ammonia and nitrogen gas, nor a sulfur containing gas. Moreover, for certain preferred embodiments in which a composition comprising an at least partially fluorinated compound comprising at least one silane group will be applied, it is desirable that the diamond-like glass coating is substantially free or free of amine functional groups and substantially free or free of amido functional groups as well as substantially free or free of thiol functional groups so as to minimize or avoid formation of silicon-nitrogen or silicon-sulfur bonds, said bonds having been determined to be undesirable in terms of durability and/or robustness of the coating system over the life of medicinal inhalation devices. Accordingly in preferred embodiments, the non-metal/diamond-like glass coating is advantageously substantially free of nitrogen (e.g., at most about 5 atomic percent of nitrogen (on a hydrogen free basis)), in particular free of nitrogen. Also in preferred embodiments, the non-metal/diamond-like glass coating is advantageously substantially free of sulfur (e.g., at most about 1 atomic percent of sulfur (on a hydrogen free basis)), in particular free of sulfur. Optionally the source gas may further comprise a source of fluorine e.g., carbon tetrafluoride. However, it is preferred not to include fluorine into the non-metal/diamond-like glass coating. The inclusion of fluorine has been determined to be generally undesirable in terms of structural integrity of the coating (in particular adhesion of the coating to the substrate surface as well as overall durability of the coating). Also for those embodiments in which a composition comprising an at least partially fluorinated compound comprising at least one functional group is applied onto the diamond-like glass coating the inclusion of fluorine is undesirable in terms of adhesion of the applied fluorine-containing composition onto the non-metal/diamond-like glass coating. Thus in preferred embodiments of the present invention, the non-metal/diamond-like glass coating is advantageously substantially free of fluorine (e.g., at most about 1 atomic percent of fluorine (on a hydrogen free basis)), in particular free of fluorine.

The source gas may further comprise oxygen gas e.g., as an assist gas. In this case, the amount of oxygen gas is less than 35% on a molar basis, in particular less than 30% on a molar basis.

To facilitate the desired production of an oxygen-lean diamond-like glass coating, in the event the source gas comprises oxygen gas and/or an organosilicon compound including oxygen atoms, it is favorable to maintain an atomic ratio of oxygen (O) to silicon (Si) (O:Si) in the source gas at a level equal to or less than 3:1, in particular equal to or less than 2.5:1, more particular at a level equal to or less than 1:1, most particularly equal to or less than 0.8:1. More favorably the source gas is substantially free or free of an oxygen assist gas.

Similarly it is desirable that the source gas is substantially free or free of oxygen-containing organosilicons. (Substantially free means that the amount of oxygen assist gas or oxygen-containing organosilicon(s) is no more than that corresponding to 5% on an atomic basis of oxygen relative to total content of silicon on an atomic basis.)

Plasma deposition of the non-metal/diamond-like glass coating typically occurs at a rate ranging from about 1 to about 100 nm/second. The rate will depend on conditions including pressure, power, concentration of gas, types of gases, relative size of the electrodes, and so on. In general, the deposition rate increases with increasing power, pressure, and concentration of gas, although the rate can approach an upper limit. Desirably plasma deposition is carried out for a period of time such that the deposited diamond-like glass coating has a thickness in the range from about 5 nm to about 5000 nm. To further facilitate expansibility it has been found desirable to provide a non-metal/diamond-like glass coating having a thickness greater than 100 nm, more desirably a thickness equal to or greater than 250 nm, most desirably a thickness greater than 550 nm. Generally the non-metal/diamond-like glass coatings have a thickness equal to or less than 5000 nm, in particular a thickness equal to or less than 3500 nm, more particularly a thickness equal to or less than 2500 nm, most particularly a thickness equal to or less than 2000 nm.

For certain, favorable embodiments, diamond-like glass coating may be used alone, e.g., free of a fluorine-containing over-coating, in particular free of an over-coating. For such certain embodiments, methods of making a medicinal inhalation device or making a component of a medicinal inhalation device are favorably free of a step of applying a fluorine-containing over-coating, more favorably free of applying an over-coating, onto the surface of the diamond-like glass coating. For such favorable embodiments, the coating may be desirably used in its native, deposited state.

Alternatively, after deposition the diamond-like glass coating may be subjected to a post surface treatment. If a post surface treatment is performed, desirably such treatment does not substantially increase the surface energy of the deposited coating and/or generate reactive groups on the surface of the deposited coating. For example, at least a portion of a surface of the formed non-metal/diamond-like glass coating (preferably the entire surface of the formed non-metal/diamond-like glass coating) may be exposed to fluorine-containing-gas plasma, under ion bombardment conditions. The fluorine-containing-gas-plasma may favorably comprise a fluorine-containing compound selected from the group consisting of fluorine ($F_2$); nitrogentrifluoride ($NF_3$); sulfurhexafluoride ($SF_6$); silicontetrafluorine ($SiF_4$); phosphorustrifluoride ($PF_3$); carbon tetrafluoride ($CF_4$); perfluoroethane ($C_2F_6$); perfluoropropane ($C_3F_8$), perfluorobutane ($C_4F_{10}$) and perfluoropentane ($C_5F_{12}$) and their isomeric forms; hexafluoropropylene (HFP) trimer; 2,2,3-trifluoro-3-(trifluoromethyl) oxirane ($C_3F_6O$); and mixtures thereof. The aforesaid "hexafluoropropylene (HFP) trimer" is to be understood to include mixtures of perfluoro-2,3,5-trimethyl 3-hexene, perfluoro-2,3,5-trimethyl 2-hexene and perfluoro-2,4,5-trimethyl 2-hexene (such mixtures are commercially available from 3M Company).

Or alternatively in certain embodiments, a composition comprising an at least partially fluorinated compound may be advantageously applied to at least a portion of a surface of the non-metal/diamond-like glass coating (preferably to the entire surface of the formed non-metal/diamond-like glass coating). In such embodiments, desirably the at least partially fluorinated compound comprises at least one functional group.

In regard to the latter alternative, desirably the non-metal/diamond-like glass coating comprises at least one functional group, where the at least one functional group is capable of forming a covalent bond with the at least one functional group of the at least partially fluorinated compound. The term "at least one functional group" as used herein is to be generally understood to include as a preferred embodiment "a plurality of functional groups". The at least one functional group of the non-metal/diamond-like glass coating desirably includes an active hydrogen. The at least one functional group may be a hydroxyl group (—OH), a thiol group (—SH), an amine group (—NH— or —NH$_2$), a carboxyl group (—COOH), an amide group (—CONH— or —CONH$_2$) or a mixture of such groups; favorably a hydroxyl group, a carboxyl group or a mixture of such groups; and more favorably a hydroxyl group. The non-metal/diamond-like glass coating may be provided with the at least one functional group upon its formation through plasma deposition under ion bombardment conditions, or alternatively (and more favorably) the coating already plasma deposited under ion bombardment conditions, may be provided with the at least one functional group through a subsequent treatment. Due to desirable high atomic packing densities of non-metal/diamond-like glass coatings plasma deposited under ion bombardment conditions, such coatings allow for the provision of a dense distribution and high number of functional groups, such as functional groups having an active hydrogen (e.g., hydroxyl groups (—OH) and/or carboxyl groups (—COOH), in particular hydroxyl groups) for subsequent bonding upon application of said composition comprising at least partially fluorinated compound comprising an at least one functional group.

Favorably, the surface of the non-metal/diamond like-glass coating is exposed to an oxygen plasma and/or water vapor, more favorably exposed to an oxygen plasma and/or water vapor under ion bombardment conditions (for example in order to form or to form additional silanol groups on the surface). Such a treatment (depending on the particular composition of the non-metal/diamond-like glass coating) generally advantageously allows for the provision of a coating with at least one functional group. For such a treatment, pressures at the surface are typically maintained between 10 mTorr (1.4 Pa) and 2000 mTorr (286 Pa), oxygen flow density is greater than 0.1 sccm/square cm, and power density is greater than 0.1 watts/square cm. Alternatively, the non-metal/diamond-like glass coating may be favorably exposed to a corona treatment prior to applying the composition comprising the at least partially fluorinated compound comprising at least one functional group.

Desirably the at least partially fluorinated compound includes a polyfluoropolyether segment, preferably a perfluorinated polyfluoropolyether segment, for enhanced surface properties as well as enhanced coating efficiency and structural integrity. The use of polyfluoropolyether segments including perfluorinated repeating units including short chains of carbon, where desirably the number of carbon atoms in sequence is at most 6, more desirably at most 4, even more desirably at most 3, and most desirably at most 2, facilitates durability/flexibility of the applied fluorine-containing coating as well as minimizing a potential of bioaccumulation of perfluorinated moieties.

Desirably the at least one functional group of the at least partially fluorinated compound includes a hydrolyzable group (e.g., hydrolyzable in the presence of water, optionally under acidic or basic conditions producing groups capable of undergoing a condensation reaction (for example silanol groups)).

Desirably the at least one functional group of the at least partially fluorinated compound is a silane group.

Favorably the silane group includes at least one hydrolyzable group, more favorably at least two hydrolyzable groups, and most favorably three hydrolyzable groups. The hydrolyzable groups may be the same or different.

Desirably a hydrolyzable group is a group selected from the group consisting of hydrogen, halogen, alkoxy, acyloxy, aryloxy, and polyalkyleneoxy, more desirably a group selected from the group consisting of alkoxy, acyloxy, aryloxy, and polyalkyleneoxy, even more desirably a group selected from the group consisting of alkoxy, acyloxy and aryloxy, and most desirably an alkoxy group (e.g., OR' wherein each R' is independently a $C_{1-6}$ alkyl, in particular a $C_{1-4}$ alkyl).

Desirably the at least partially fluorinated compound comprising at least one functional group is a polyfluoropolyether silane, more desirably a multifunctional polyfluoropolyether silane, and most desirably a difunctional polyfluoropolyethersilane.

It has been found that the use of compositions comprises a multifunctional polyfluoro-polyether silane (in particular a difunctional polyfluoropolyethersilane) and a monofunctional polyfluoropolyethersilane is particularly favorable.

The term "multifunctional polyfluoropolyether silane" as used herein is generally understood to mean a multivalent polyfluoropolyether segment functionalized with a multiple of functional silane groups, and the term "difunctional polyfluoropolyether silane" as used herein is generally understood to mean a divalent polyfluoropolyether segment functionalized with a multiple of functional silane groups (in particular two to four functional silane groups, more particularly two functional silane groups). The term "monofunctional polyfluoropolyether silane" as used herein is generally understood to mean a monovalent polyfluoropolyether segment functionalized with one or more functional silane groups (in particular one functional silane group or two functional silane groups).

It has been found that the use of a multifunctional polyfluoropolyether silane, in particular a difunctional polyfluoropolyether silane, allows for high application efficiency and coverage as well as extensive bonding (covalent bonding) to the diamond-like glass coating as well as cross-linking within the fluorine containing coating itself thus facilitating structural integrity of the applied fluorine-containing coating. And a multifunctional polyfluoropolyether silane in conjunction with a monofunctional polyfluoropolyether silane provides in addition highly desirable surface characteristics.

For enhanced stability and/or resistance to attack (e.g., by ethanol, drug, and/or other potential components of medicinal inhalation formulations) desirably polyfluoropolyether segment(s) is (are) not linked to silane group(s) via a functionality that includes a nitrogen-silicon bond or a sulfur-silicon bond. In particular, for enhanced stability and resistance of the applied fluorine-containing coating to attack, it is desirable that polyfluoropolyether segment(s) is (are) linked to silane group(s) via a functionality that includes a carbon-silicon bond, more particularly via a —C(R)$_2$—Si functionality where R is independently hydrogen or a $C_{1-4}$ alkyl group (preferably hydrogen), and most particularly, via a —(C(R)$_2$)$_k$—C(R)$_2$—Si functionality where k is at least 2 (preferably 2 to about 25, more preferably 2 to about 15, most preferably 2 to about 10). The inclusion of —(C(R)$_2$)$_k$— where k is at least 2 advantageously, additionally provides flexural strength Favorably, the at least partially fluorinated compound comprising at least one silane group is a polyfluoropolyether silane of the Formula Ia:

$$R_f[Q\text{-}[C(R)_2\text{---}Si(Y)_{3\text{-}x}(R^{1a})_x]_y]_z \quad \text{Ia}$$

wherein:
  $R_f$ is a monovalent or multivalent polyfluoropolyether segment;
  Q is an organic divalent or trivalent linking group;
  each R is independently hydrogen or a $C_{1\text{-}4}$ alkyl group;
  each Y is independently a hydrolyzable group;
  $R^{1a}$ is a $C_{1\text{-}8}$ alkyl or phenyl group;
  x is 0 or 1 or 2;
  y is 1 or 2; and
  z is 1, 2, 3, or 4.

Application of polyfluoropolyether silanes in accordance with Formula Ia favorably allows the provision of medicinal inhalation devices or components thereof comprising a non-metal/diamond-like glass coating on at least a portion of surface of the device or component, as applicable, and a polyfluoropolyether-containing coating bonded to the non-metal/diamond-like glass coating, wherein the polyfluoropolyether-containing coating comprises polyfluoropolyether silane entities of the following Formula Ib:

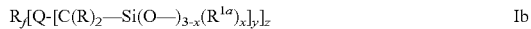

$$R_f[Q\text{-}[C(R)_2\text{---}Si(O\text{---})_{3\text{-}x}(R^{1a})_x]_y]_z \quad \text{Ib}$$

which shares at least one covalent bond with the non-metal/diamond-like glass coating; and
wherein:
  $R_f$ is a monovalent or multivalent polyfluoropolyether segment;
  Q is an organic divalent or trivalent linking group;
  each R is independently hydrogen or a $C_{1\text{-}4}$ alkyl group;
  $R^{1a}$ is a $C_{1\text{-}8}$ alkyl or phenyl group;
  x is 0 or 1 or 2;
  y is 1 or 2; and
  z is 1, 2, 3, or 4.

Advantageously the at least one covalent bond shared with the non-metal/diamond-like glass coating is a bond to an oxygen atom in $Si(O\text{---})_{3\text{-}x}$. Favorably such polyfluoropolyether-containing coatings are typically transparent or translucent.

The monovalent or multivalent polyfluoropolyether segment, $R_f$, includes linear, branched, and/or cyclic structures, that may be saturated or unsaturated, and includes two or more in-chain oxygen atoms. $R_f$ is preferably a perfluorinated group (i.e., all C—H bonds are replaced by C—F bonds). However, hydrogen atoms may be present instead of fluorine atoms provided that not more than one atom of hydrogen is present for every two carbon atoms. When hydrogen atoms are present, preferably, $R_f$ includes at least one perfluoromethyl group.

For certain embodiments, the monovalent or multivalent polyfluoropolyether segment, $R_f$, comprises perfluorinated repeating units selected from the group consisting of —$(C_nF_{2n})$—, —$(C_nF_{2n}O)$—, —$(CF(Z))$—, —$(CF(Z)O)$—, —$(CF(Z)C_nF_{2n}O)$—, —$(C_nF_{2n}CF(Z)O)$—, —$(CF_2CF(Z)O)$—, and combinations thereof wherein n is an integer from 1 to 6; Z is a perfluoroalkyl group, an oxygen-containing perfluoroalkyl group, a perfluoroalkoxy group, or an oxygen-substituted perfluoroalkoxy group, each of which can be linear, branched, or cyclic, and have 1 to 5 carbon atoms and up to 4 oxygen atoms when oxygen-containing or oxygen-substituted. For units comprising Z it is desirable that the total number of carbon atoms in sequence per unit is at most 6 (more desirably at most 4, and most desirably at most 3). Being oligomeric or polymeric in nature, these compounds exist as mixtures and are suitable for use as such. The perfluorinated repeating units may be arranged randomly, in blocks, or in an alternating sequence. Favorably, the polyfluoropolyether segment comprises perfluorinated repeating units selected from the group consisting of —$(C_nF_{2n}O)$—, —$(CF(Z)O)$—, —$(CF(Z)C_nF_{2n}O)$—, —$(C_nF_{2n}CF(Z)O)$—, —$(CF_2CF(Z)O)$—, and combinations thereof; and more favorably perfluorinated repeating units selected from the group consisting of —$(C_nF_{2n}O)$—, —$(CF(Z)O)$—, and combinations thereof. For certain of these embodiments, n is an integer from 1 to 4; or 1 to 3; or 1 or 2. For certain of these embodiments, Z is a —$CF_3$ group.

For certain embodiments, including any one of the above embodiments, $R_f$ is monovalent, and z is 1. For certain of these embodiments, $R_f$ is terminated with a group selected from the group consisting of $C_nF_{2n+1}$—, $C_nF_{2n+1}O$—, and X'$C_nF_{2n}O$— wherein X' is a hydrogen. For certain of these embodiments, the terminal group is $C_nF_{2n+1}$— or $C_nF_{2n+1}O$— wherein n is an integer from 1 to 6 or 1 to 3. For certain of these embodiments, the approximate average structure of $R_f$ is $C_3F_7O(CF(CF_3)CF_2O)_pCF(CF_3)$—, $CF_3O(C_2F_4O)_pCF_2$—, $C_3F_7O(CF(CF_3)CF_2O)_pCF_2CF_2$—, $C_3F_7O(CF_2CF_2CF_2O)_pCF_2CF_2$—, or $C_3F_7O(CF_2CF_2CF_2O)_pCF(CF_3)$—, or $CF_3O(CF_2CF(CF_3)O)_p(CF_2O)X$— (wherein X is $CF_2$—, $C_2F_4$—, $C_3F_6$—, or $C_4F_8$—) wherein the average value of p is 3 to 50.

For enhanced application efficiency and coverage as well as extensive bonding to non-metal/diamond-like glass coating and inter-linking within the fluorine-containing coating itself, thus facilitating a high structural integrity of the applied fluorine-containing coating, $R_f$ is preferably multivalent and z is 2, 3 or 4, more preferably $R_f$ is divalent, and z is 2. For certain of these embodiments, the approximate average structure of $R_f$ is selected from the group consisting of —$CF_2O(CF_2O)_m(C_2F_4O)_pCF_2$—, —$CF_2O(C_2F_4O)_pCF_2$—, —$CF(CF_3)O(CF(CF_3)CF_2O)_pCF(CF_3)$—, —$(CF_2)_3O(C_4F_8O)_p(CF_2)_3$—, —$CF(CF_3)$—$(OCF_2CF(CF_3))_pO$—$C_tF_{2t}$—$O(CF(CF_3)CF_2O)_pCF(CF_3)$— (wherein t is 2 to 4), and wherein m is 1 to 50, and p is 3 to 40. For certain of these embodiments, $R_f$ is selected from the group consisting of —$CF_2O(CF_2O)_m(C_2F_4O)_pCF_2$—, —$CF_2O(C_2F_4O)_pCF_2$—, and —$CF(CF_3)$—$(OCF_2CF(CF_3))_pO$—$(C_tF_{2t})$—$O(CF(CF_3)CF_2O)_pCF(CF_3)$—, and wherein t is 2, 3 or 4, and the average value of m+p or p+p or p is from about 4 to about 24.

The above structures are approximate average structures where p and m designate the number of randomly distributed perfluorinated repeating units. Further, polyfluoro-polyether silanes, such as those described above, also typically include a distribution of oligomers and/or polymers, so p and/or m may be non-integral and where the number is the approximate average over this distribution.

The organic divalent or trivalent linking group, Q, can include linear, branched, or cyclic structures that may be saturated or unsaturated. The organic divalent or trivalent linking group, Q, optionally contains one or more heteroatoms selected from the group consisting of sulfur, oxygen, and nitrogen, and/or optionally contains one or more functional groups selected from the group consisting of esters, amides, sulfonamides, carbonyl, carbonates, ureylenes, and carbamates. Again for flexural strength Q favorably includes a segment with not less than 2 carbon atoms, said segment of Q being directly bonded to the —$C(R)_2$— group of the silane-containing moiety (i.e., for Formula Ia —$C(R)_2$—$Si(Y)_{3\text{-}x}(R^{1a})_x$ and for Formula Ib —$C(R)_2$—$Si(O\text{---})_{3\text{-}x}(R^{1a})_x$). For such embodiments generally Q includes not more than about 25 carbon atoms. Q is preferably substantially stable against hydrolysis and other chemical transformations, such as nucleophilic attack. When more than one Q group is present, the Q groups can be the same or different.

For certain embodiments, including any one of the above embodiments, Q includes organic linking groups such as $—C(O)N(R)—(CH_2)_k—$, $—S(O)_2N(R)—(CH_2)_k—$, $—(CH_2)_k—$, $—CH_2O—(CH_2)_k—$, $—C(O)S—(CH_2)_k—$, $—CH_2OC(O)N(R)—(CH_2)_k—$, and

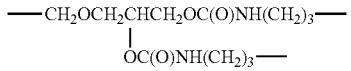

wherein R is hydrogen or $C_{1-4}$ alkyl, and k is 2 to about 25. For certain of these embodiments, k is 2 to about 15 or 2 to about 10.

Favorably Q is a divalent linking group, and y is 1. In particular, Q is favorably a saturated or unsaturated hydrocarbon group including 1 to about 15 carbon atoms and optionally containing 1 to 4 heteroatoms and/or 1 to 4 functional groups. For certain of these embodiments, Q is a linear hydrocarbon containing 1 to about 10 carbon atoms, optionally containing 1 to 4 heteroatoms and/or 1 to 4 functional groups. For certain of these embodiments, Q contains one functional group. For certain of these embodiments, Q is preferably $—C(O)N(R)(CH_2)_2—$, $—OC(O)N(R)(CH_2)_2—$, $—CH_2—O—(CH_2)_2—$, or $—CH_2—OC(O)N(R)—(CH_2)_2—$, wherein R is hydrogen or $C_{1-4}$ alkyl.

For certain embodiments, including any one of the above embodiments, where R is present R is hydrogen.

The hydrolyzable groups, Y, of Formula Ia may be the same or different and are capable of hydrolyzing, for example, in the presence of water, optionally under acidic or basic conditions, producing groups capable of undergoing a condensation reaction, for example silanol groups. For example, methoxy and ethoxy groups form essentially immediately "in situ" (e.g., in the presence of water) hydroxy groups, so that silanol groups are generated.

Desirably, each Y of Formula Ia is independently a group selected from the group consisting of hydrogen, halogen, alkoxy, acyloxy, aryloxy, and polyalkyleneoxy, more desirably each Y is independently a group selected from the group consisting of alkoxy, acyloxy, aryloxy, and polyalkyleneoxy, even more desirably each Y is independently a group selected from the group consisting of alkoxy, acyloxy and aryloxy, and most desirably each Y is independently an alkoxy group.

For certain embodiments, including any relevant embodiment described herein:

Favorably alkoxy is —OR', and acyloxy is —OC(O)R', wherein each R' is independently a lower alkyl group, optionally substituted by one or more halogen atoms. For certain embodiments, R' is preferably $C_{1-6}$ alkyl and more preferably $C_{1-4}$ alkyl. R' can be a linear or branched alkyl group.

Favorably aryloxy is —OR" wherein R" is aryl optionally substituted by one or more substituents independently selected from halogen atoms and $C_{1-4}$ alkyl optionally substituted by one or more halogen atoms. For certain embodiments, R" is preferably unsubstituted or substituted $C_{6-12}$ aryl and more preferably unsubstituted or substituted $C_{6-10}$ aryl.

Favorably polyalkyleneoxy is $—O—(CHR^4—CH_2O)_q—R^3$ wherein $R^3$ is $C_{1-4}$ alkyl, $R^4$ is hydrogen or methyl, with at least 70% of $R^4$ being hydrogen, and q is 1 to 40, preferably 2 to 10.

For certain embodiments, including any one of the above embodiments, x is 0.

For certain embodiments, including any one of the above embodiments including a compound in accordance with Formula Ia, $R_f$ is $—CF_2O(CF_2O)_m(C_2F_4O)_pCF_2—$ and $Q\text{-}C(R)_2—Si(Y)_{3-x}(R^{1a})_x$ is $C(O)NH(CH_2)_3Si(OR')_3$, in particular wherein R' is methyl or ethyl. For certain embodiments, including any one of the above embodiments including an entity in accordance with Formula Ib, $R_f$ is $—CF_2O(CF_2O)_m(C_2F_4O)_pCF_2—$ and $Q\text{-}C(R)_2—Si(O—)_{3-x}(R^{1a})_x$ is $C(O)NH(CH_2)_3Si(O—)_3$. For certain of these embodiments, m+p or p is from about 4 to about 24, more particularly m and p are each about 9 to about 12.

For certain embodiments, including any one of the above embodiments including a compound in accordance with Formula Ia, $R_f$ is $C_3F_7O(CF(CF_3)CF_2O)_pCF(CF_3)—$, and $Q\text{-}C(R)_2—Si(Y')_{3-x}(R^{1a})_x$ is $C(O)NH(CH_2)_3Si(OR')_3$, in particular wherein R' is methyl or ethyl. For certain embodiments, including any one of the above embodiments including an entity in accordance with Formula Ib, $R_f$ is $C_3F_7O(CF(CF_3)CF_2O)_pCF(CF_3)—$ and $Q\text{-}C(R)_2—Si(O—)_{3-x}(R^{1a})_x$ is $C(O)NH(CH_2)_3Si(O—)_3$. For certain of these embodiments, p is from about 3 to about 20, more particularly from about 4 to about 10.

It has been surprisingly found that two aforesaid compounds in accordance with Formula Ia in combination provide fluorine-containing coatings showing unexpectedly significantly better performance, e.g., in regard to deposition of salbutamol sulfate, than coatings made based on each of the individual compounds. Accordingly embodiments of methods described herein favorably including applying a composition comprising an at least partially fluorinated compound to at least a portion of a surface of the non-metal/diamond-like glass coating, the composition advantageously comprises at least the following two polyfluoropolyether silanes in accordance with Formula Ia:

(a) a first polyfluoropolyether silane wherein $R_f$ is $C_3F_7O(CF(CF_3)CF_2O)_pCF(CF_3)—$, and $Q\text{-}C(R)_2—Si(Y')_{3-x}(R^{1a})_x$ is $C(O)NH(CH_2)_3Si(OR')_3$ (in particular wherein R' is methyl or ethyl) wherein p is 3 to 50, in particular wherein p is from about 3 to about 20, more particularly p is from about 4 to about 10; and (b) a second polyfluoropolyether silane wherein $R_f$ is $—CF_2O(CF_2O)_m(C_2F_4O)_pCF_2—$, and $Q\text{-}C(R)_2—Si(Y')_{3-x}(R^{1a})_x$ is $C(O)NH(CH_2)_3Si(OR')_3$, (in particular wherein R' is methyl or ethyl) wherein m is 1 to 50 and p is 3 to 40, in particular wherein the average value of m+p or p is from about 4 to about 24, more particularly wherein m and p are each about 9 to about 12.

Desirably the composition comprises a catalyst and the composition comprises at least a total of 0.1 wt % of said first and second polyfluoropolyether silanes, in particular at least a total of 0.5 wt % of said first and second polyfluoropolyether silanes, more particularly at least a total of one (1) wt % of said first and second polyfluoropolyether silanes. Or alternatively the composition is free of catalyst and the composition comprises at least a total of one (1) wt % of said first and second polyfluoropolyether silanes, in particular at least a total of 2.5 wt % of said first and second polyfluoropolyether silanes, more particularly at least a total of 5 wt % of said first and second polyfluoropolyether silanes. Favorably the weight percent ratio of the first to second polyfluoropolyether silane (first polyfluoropolyether silane:second polyfluoropolyether silane) in the composition is equal to or greater than 10:90, in particular equal to or greater than 20:80, more particularly equal to or greater than 30:70, most particularly equal to or greater than 40:60. Desirably the weight percent ratio of the first to second polyfluoropolyether silane (first polyfluoropolyether silane:second polyfluoropolyether silane) in the composition is equal to or less than 99:1, in particular equal to or less than 97:3, most particularly equal to or less than 95:5.

Compounds of Formula Ia described above can be synthesized using standard techniques. For example, commercially available or readily synthesized polyfluoropolyether esters (or functional derivatives thereof) can be combined with a functionalized alkoxysilane, such as a 3-aminopropylalkoxysilane, according to U.S. Pat. No. 3,810,874 (Mitsch et al.).

For certain embodiments, the weight average molecular weight of the polyfluoropolyether segment is about 900 or higher, more desirably about 1000 or higher. Higher weight average molecular weights further facilitate durability as well as minimizing a potential of bioaccumulation. Generally for ease in use and application, the weight average molecular weight of the polyfluoropolyether segment is desirably about 6000 at most and more desirably about 4000 at most, most desirably about 3000 at most.

Polyfluoropolyether silanes, as indicated above, typically include a distribution of oligomers and/or polymers. Desirably for facilitation of the structural integrity of the polyfluoropolyether-containing coating as well as minimization of a potential of bioaccumulation, the amount of polyfluoropolyether silane (in such a distribution) having a polyfluoropolyether segment having a weight average molecular weight less than 750 is not more than 10% by weight (more desirably not more than 5% by weight, and even more desirably not more 1% by weight and most desirably 0%) of total amount of polyfluoropolyether silane in said distribution.

For certain embodiments, including any one of the above embodiments, the composition comprising an at least partially fluorinated compound comprising at least one functional group further includes an organic solvent.

For certain embodiments, including any one of the above embodiments wherein the at least partially fluorinated compound comprising at least one functional group is a polyfluoropolyether silane, the polyfluoropolyether silane is desirably applied as a composition comprising the polyfluoropolyether silane and an organic solvent. The organic solvent or blend of organic solvents used typically is capable of dissolving at least about 0.01 percent by weight of the polyfluoropolyether silane, in particular one or more silanes of the Formula Ia. It is desirable that the solvent or mixture of solvents have a solubility for water of at least about 0.1 percent by weight, and for certain of these embodiments, a solubility for acid of at least about 0.01 percent by weight.

Suitable organic solvents, or mixtures of solvents can be selected from aliphatic alcohols, such as methanol, ethanol, and isopropanol; ketones such as acetone and methyl ethyl ketone; esters such as ethyl acetate and methyl formate; ethers such as diethyl ether, diisopropyl ether, methyl t-butyl ether and dipropyleneglycol monomethylether (DPM); hydrocarbon solvents such as alkanes, for example, heptane, decane, and paraffinic solvents; fluorinated hydrocarbons such as perfluorohexane and perfluorooctane; partially fluorinated hydrocarbons, such as pentafluorobutane; hydrofluoroethers such as methyl perfluorobutyl ether and ethyl perfluorobutyl ether. For certain embodiments, including any one of the above embodiments, the organic solvent is a fluorinated solvent, which includes fluorinated hydrocarbons, partially fluorinated hydrocarbons, and hydrofluoroethers. For certain of these embodiments, the fluorinated solvent is a hydrofluoroether. For certain of these embodiments, the hydrofluoroether is methyl perfluorobutyl ether and/or ethyl perfluorobutyl ether. For certain embodiments, including any one of the above embodiments except where the organic solvent is a fluorinated solvent, the organic solvent is a lower alcohol. For certain of these embodiments, the lower alcohol is selected from the group consisting of methanol, ethanol, isopropanol, and mixtures thereof. For certain of these embodiments, the lower alcohol is ethanol.

For certain embodiments, including any one of the above embodiments where the organic solvent is a lower alcohol and the composition comprises an at least partially fluorinated compound comprising at least one silane group, the composition favorably further comprises an acid. For certain of these embodiments, the acid is selected from the group consisting of acetic acid, citric acid, formic acid, triflic acid, perfluorobutyric acid, sulfuric acid, and hydrochloric acid. For certain of these embodiments, the acid is hydrochloric acid.

The composition comprising an at least partially fluorinated compound comprising at least one functional group may favorably further comprise a non-fluorinated cross-linking agent that is capable of engaging in a cross-linking reaction. Preferably such a cross-linking agent comprises one or more non-fluorinated compounds, each compound having at least two hydrolyzable groups. Advantageously such a cross-linking agent comprises one or more non-fluorinated compounds of silicon having at least two hydrolyzable groups per molecule. Preferably the hydrolyzable groups are directly bonded to the silicon in accordance to Formula II:

$$Si(Y^2)_{4-g}(R^5)_g \qquad \text{II}$$

where $R^5$ represents a non-hydrolyzable group;
$Y^2$ represents a hydrolyzable group; and
g is 0, 1 or 2.

The non-hydrolyzable group $R^5$ is generally not capable of hydrolyzing under the conditions used during application of the composition comprising the at least partially fluorinated compound comprising at least one functional group. For example, the non-hydrolyzable group $R^5$ may be independently selected from a hydrocarbon group. If g is 2, the non-hydrolyzable groups may the same or different. Preferably g is 0 or 1, more preferably g is 0. The hydrolyzable groups $Y^2$ may be the same or different and are generally capable of hydrolyzing under appropriate conditions, for example under acidic or basic aqueous conditions, such that the cross-linking agent can undergo condensation reactions. Preferably, the hydrolyzable groups upon hydrolysis yield groups, such as silanol groups capable of undergoing condensation reactions. Typical and preferred examples of hydrolyzable groups include those as described with respect to Formula Ia. Preferably, $Y^2$ is an alkoxy, $-OR^6$, more preferably an alkoxy where $R^6$ is a $C_{1-4}$ alkyl.

Representative examples of favorable non-fluorinated silicon compounds for use in a cross-linking agent include tetramethoxysilane, tetraethoxysilane, tetrapropoxysilane, tetrabutoxysilane, methyl triethoxysilane, dimethyldiethoxysilane, octadecyltriethoxy-silane, 3-glycidoxypropyltriethoxysilane, 3-aminopropyltrimethoxysilane, 3-aminopropyl-triethoxysilane, 3-trimethoxysilylpropyl-methacrylate and mixtures thereof. Preferably the cross-linking agent comprises $C_1$-$C_4$ tetra-alkoxy derivatives of silicon, more preferably the cross-linking agent comprises tetraethoxysilane.

The amounts by weight of the at least partially fluorinated compound to the non-fluorinated cross-linking agent can change from about 10:1 to about 1:100, preferably from about 1:1 to about 1:50 and most preferably from about 1:2 to about 1:20.

For certain embodiments, e.g., compositions including a hydrolyzable group, the composition may further comprise water.

The composition comprising an at least partially fluorinated compound comprising at least one functional group (in particular one silane group), including any one of the above embodiments, can be applied to at least a portion of the surface (preferably the entire surface) of the non-metal/diamond-like glass coating using a variety of coating methods. Such methods include but are not limited to spraying, dipping, spin coating, rolling, brushing, spreading and flow coating. Preferred methods for application include spraying and dipping. For certain embodiments, including any one of the above embodiments, the composition comprising an at least partially fluorinated compound comprising at least one functional group, in any one of its above described embodiments, is applied by dipping at least a portion of the substrate upon which the non-metal/diamond-like glass coating has been formed in said composition. Alternatively, for certain embodiments, including any one of the above embodiments, the composition comprising the at least partially fluorinated compound comprising at least one functional group, including any one of its above described embodiments, is applied by spraying at least a portion of the substrate upon which the non-metal/diamond-like glass coating has been formed with said composition.

In preferred embodiments the diamond-like glass coating includes active functional groups on its surface, such as —SiOH (either provided during its forming or, more favorably and typically, via a post-treatment as described above) so that upon application of the composition comprising an at least partially fluorinated compound comprising at least one silane group (in particular a polyfluoropolyether silane or more particularly any one of the embodiments of Formula Ia) an extremely durable coating is formed through the formation of covalent bonds, including bonds in Si—O—Si groups. Favorably the fluorine-containing coating is covalently bonded to the diamond-like glass coating through a plurality of covalent bonds, more favorably through covalent bonds including bonds in O—Si groups, more desirably including bonds in Si—O—Si groups For the preparation of such a durable coating, sufficient water should be present to cause hydrolysis of the hydrolyzable groups described above so that condensation to form Si—O—Si groups takes place, and thereby curing takes place. The water can be present either in the treating composition or adsorbed to the substrate surface, for example. Typically, sufficient water is present for the preparation of a durable coating if the application is carried out at room temperature in an atmosphere containing water, for example, an atmosphere having a relative humidity of about 30% to about 80%.

Application is typically carried out by contacting the substrate with the treating composition, generally at room temperature (typically about 20° C. to about 25° C.). Alternatively the treating composition can be applied to a substrate that is pre-heated at a temperature of for example between 60° C. and 150° C. Following application the treated substrate can be dried and cured at ambient temperature or (preferably) at elevated temperatures (e.g., at 40° C. to 300° C.), and for a time sufficient to dry and cure. If desired or needed, the treating composition may further comprise a thermal initiator.

Alternatively or in addition thereto, following application of the treating composition the treated substrate may be cured (again if desired or needed) by irradiation (e.g., means of UV-irradiators, etc.). Hereto the treating composition typically further comprises a photo-initiator, and curing is performed in a manner known per se, depending on the type and presence, respectively of the photo-initiator used in the treating composition.

A post-treatment process may include a rinsing step (e.g., before or after drying/curing, as desired or needed) to remove excess material, followed by a drying step.

Generally the thickness of the fluorine-containing coating is favorably greater than a monolayer and thus is greater than 15 Angstroms. Preferably the thickness of the fluorine-containing coating is at least about 2 nm, preferably at least about 10 nm, even more preferably at least about 25 nm, and most preferably at least about 40 nm. For certain of these embodiments, the thickness is at most about 200 nm, preferably at most about 150 nm, and most preferably at most about 100 nm.

For embodiments described herein including a diamond-like glass coating and a fluorine-containing over-coating, the combined thickness of the two coats may be about 100 nm up to about 5200 nm. Favorably the combined thickness of the two coats is about 252 nm or higher, more favorably greater than about 552 nm. Favorably the combined thickness of the two coats is about 3700 nm or lower, more favorably about 2700 nm or lower, most favorably about 2200 nm or lower.

Additional aspects of the present invention include: devices and components made in accordance with aforesaid methods.

Besides the provision of medicinal inhalation devices and components thereof having desirable surface properties and structural integrity, methods of providing such medicinal inhalation devices and components as described herein are advantageous in their versatility and/or broad applicability to making various components of such medicinal inhalation devices, such components having significantly differing shapes and forms made of significantly differing materials. For example methods described herein can be advantageously used to provide a coating on at least a portion of the interior surface (preferably on the entire interior surface, more preferably the entire surface) of an MDI aerosol container, in particular a conventional MDI aerosol container made of aluminum or an aluminum alloy as well as MDI aerosol containers made of other metals, such as stainless steel, as well as other materials such as glass, ceramic, plastics. The latter is particularly interesting in that the methods described herein and/or the application of diamond-like glass coatings described herein may allow for the provision of plastic aerosol containers having favorable properties for commercial use. Methods described herein can also be advantageously used to provide a coating on at least a portion of a surface (preferably the entire surface) of a valve stem or a valve body, in particular a valve stem or a valve body made of a polymer such as PBT or acetal. In fact the same method (chemicals, process conditions, etc.) with little or no modification can be used to coat aluminum or aluminum alloy MDI containers and metal and/or polymeric valve stems and valve bodies (typically stainless steel and/or PBT and/or acetal) as well as compression springs (typically made of stainless steel) and actuators (typically made of polyethylene or polypropylene). This is particularly advantageous for large scale manufacturing and coating as well as stream-lining of manufacturing processing, facilities and/or equipment for coating, while at the same time allowing freedom in regard to the selection of the base material of a component and in some instances expanding the possibilities of the base material for a component.

As detailed above, particular embodiments (in particular those embodiments including a diamond-like glass coating either alone or treated with a fluorine-containing plasma gas or over-coated with a fluorine-containing coating as described herein) have very favorable impermeability characteristics. These coatings are particular advantageous for use with DPI powder containers or carriers or MDI aerosol containers. Moreover due to their very favorable impermeability characteristics, such coatings allow the use of containers, e.g., MDI aerosol containers, made of plastic or other materials which in the past have been ruled out due to the potential of permeation of moisture from outside to the inside, permeation of aerosol formulation through or into the container material and/or extraction of container material into the aerosol formulation. Furthermore, such coatings described herein that are transparent or translucent can be used to provide a transparent or translucent plastic MDI aerosol container which can be advantageous in that a patient can easily monitor the content of the container (i.e., whether it is empty and needs to be replaced).

Methods described herein can also be used to provide other medicinal inhalation devices including nebulizers, pump spray devices, nasal pumps, non-pressurized actuators or components of such devices. Accordingly medicinal inhalation devices or components described herein may also be nebulizers, pump spray devices, nasal pumps, non-pressurized actuators or components of such devices.

Methods described herein can also be used to provide other components used in medicinal inhalation such as breath-actuating devices, breath-coordinating devices, spacers, dose counters, or individual components of such devices, spacers and counters, respectively. Accordingly components described herein may also be breath-actuating devices, breath-coordinating devices, spacers, dose counters, or individual components of such devices, spacers, counters, respectively. In regard to provision of a component or components of dose counters of medicinal inhalation devices, due to desirable surface properties and structural integrity (in particular durability and resistance to wear) of coatings described herein, the provision of such a coating on a component or components (in particular movable component(s) and/or component(s) in contact with a movable component) of a dose counter provides dry lubricity facilitating smooth operation of the dose counter.

Objects and advantages of this invention are further illustrated by the following examples, but the particular materials and amounts thereof recited in these examples, as well as other conditions and details, should not be construed to unduly limit this invention.

EXAMPLES

In all the Examples—19 milliliter, aluminum aerosol containers having generally a form as that illustrated in FIG. 1; a height (brim to base) of 59.10 mm (median value) and a neck outer diameter (at its most narrow portion) of 17.02 mm (median value) were used.

Plasma treatment as described in the following was performed unless specified otherwise Plasma Treatment Method Exemplary containers were treated in a custom-built system. The system includes an aluminum manifold having two generally horizontal chambers, one connected to a gas feed/supply system and the other to a vacuum system, and a central vertical opening with appropriate seal systems to allow for sealing-connection to a nozzle; and an insulating barrier block made of polymeric material, polyetherimide, (available under the trademark ULTEM (grade 1000) of General Electric Company and available from many suppliers worldwide) having a central vertical opening and fitted below the manifold so that the openings were aligned. The system includes a nozzle having five substantially parallel bores, a central bore and four outer bores, where the nozzle has a middle body-portion and two extensions on opposite ends, and the central bore runs through the extensions and body-portions and the outer bores run through the body-portion. One end of the nozzle is inserted through the insulating barrier block into the manifold so that the respective opening of the central bore taps into the gas feed chamber and the respective openings of the outer bores tap into the vacuum chamber. The body-portion of the nozzle is sealed within the barrier block, such that the lower surface of the body-portion and the openings of the outer bores are substantially flush with the lower surface of the barrier block and the central bore-extension extends beyond the lower surface of the body-portion of the nozzle (and the barrier block) about 44.45 mm. A sealing system is provided on the lower side of the block near the block/nozzle conjunction to allow for a sealing-connection to the container to be coated. The system is fitted with four such nozzles.

For coating, the four nozzles were lowered into four containers so that the upper edge of the brim of each container was in contact with the lower side of the nozzle-body-portion and so that a seal was created between each container (outer surface of brim) and the outer lower surface of the barrier block. Voltage was applied to the containers and the nozzles were grounded to create the plasma and an ion sheath within the interior of the container, in order to coat the interior of the containers. To provide a gas flow through the container, the containers were continuously evacuated via the outer bores (inlet openings near the brim) while gas was supplied into the containers via the central bore-extension. Plasma was powered by a 1 kW, 13.56 MHz solid-state generator (Seren, Model No. R1001, available from Seren IPS, Inc., Vineland, N.J., USA) and a radio frequency impedance matching network ($R_f$Plasma Products Model AMN-10, available from Advanced Energy, Fort Collins, Colo.). The system had a nominal base pressure of 5 mTorr (0.67 Pa). The flow rates of gases were controlled by flow controllers available from MKS Instruments Incorporated (Wilmington, Mass.).

The plasma treatment included the following steps:

Step 1. Exemplary containers were first treated in an oxygen plasma by flowing oxygen gas (99.99%, UHP Grade, available from Scott Specialty Gases, Plumsteadville, Pa.) at 50 standard cubic centimeters per minute (sccm) flow rate while maintaining within the containers a pressure within the range of 1000-1500 millitorr (mtorr) (130-200 Pascals (Pa)) and plasma power of 75 watts. The oxygen priming step was carried out for 20 seconds.

Step 2. Following the oxygen plasma priming, either oxygen flow was stopped ("0 sccm") (Example 1) or oxygen flow was maintained at a reduced flow of 5 sccm, 10 sccm, 15 sccm or 20 sccm (Examples 2 through 5, respectively), and tetramethylsilane (99.9%, NMR Grade, available from Sigma-Aldrich Chemicals, St. Louis, Mo.) was introduced at a flow rate of 25 sccm. For Examples 1-5, respectively the pressure was held within the containers within the range of 600-1000 mtorr (80-130 Pa), and plasma power was held at 75 watts. The treatment time was 180 seconds, with a corresponding deposition rate of about 100-300 nm/min.

Each step used a power density of about 0.47 watts/square cm (75 watts divided by (four cans times 40 square cm/can) (four cans treated in one run & area of interior surface of each can is about 40 $cm^2$)). Step 2 used in each case a TMS flow density of about 0.16 sccm/square cm.

Determination of Atomic Percent Data Via X-Ray Photoelectron Spectroscopy (XPS)

XPS survey spectra were recorded at randomly selected areas on the plasma-treated substrate (such as areas on the interior surface of each plasma-treated aerosol container). Said XPS data were acquired and analyzed using a Kratos Model AXIS Ultra DLD spectrometer (available Kratos Analytical Ltd, Wharfside, Manchester, UK) (Hybrid Operation mode) with a monochromatic Al—$K_a$ X-ray source and using Hybrid operation mode. The emitted photoelectrons were detected at a 90 degree take-off angle (take-off angle defining the angle between the sample surface and the axis of the XPS analyzer lens) with respect to the sample surface. A low-energy electron flood gun was used to minimize surface charging. The area analyzed for each data point was approximately 700 µm×300 µm. Pass energy for survey scan was 160 eV; scan rate 400 meV/Step; dwell time 87 ms. Three to four areas on each sample were analyzed and averaged to obtain the reported atomic % values.

Test Procedure for Evaluation of a Coating Upon Crimping

To simulate the impact of valve crimping on the plasma deposited coating within the containers, empty, coated containers were crimped with blind ferrules including a ferrule gasket and a O-ring with a crimp height of 5.9 mm (down from the brim of the container) and crimp diameter of 17.9 mm. After crimping the blind ferrules were carefully cut off at or just below ferrule gasket seal. An aqueous copper sulfate pentahydrate/hydrochloric acid solution was prepared by combining 78 g of copper(II) sulfate pentahydrate, 20 mL of 37% hydrochloric acid, and 500 mL of deionized water. Each container was filled to the brim with this solution. This solution aggressively reacts with exposed aluminum resulting in deposition of copper at exposed sites, and thus this solution allows for a visual assessment of the effect of crimping on the coating and thus the integrity of the coating during crimping. Due to inward reduction of diameter and/or strain about the neck as well as axial load that the operation of crimping places onto the container, the integrity of interior coating about the neck and about the side portion of the can near the transition between the side wall and base has been found to be particularly critical. Where the coating has cracked or has been otherwise damaged during crimping so that underlying metal is accessible, the copper sulfate/HCl test solution will cause corrosion together with a red-discoloring. One minute after filling the copper sulfate/HCl test solution into the containers, the solution was decanted from the containers, and the containers were rinsed with deionized water and allowed to air dry. After drying, the containers were sectioned to enable observation of the internal section. The containers were examined and assigned a visual attribute score as based on the following criteria:

0—no corrosion (no corrosion visible even with magnification)
1—very slight (corrosion visible with magnification)
2—slight (corrosion just visible without magnification)
3—moderate
4—significant A plurality of cans (up to 5) was examined and the reported score is the average of the scores.

Table 1 summarizes the results of the corrosion examination together with the-on-hydrogen-free-basis atomic percents of oxygen, silicon and carbon of Examples 1 to 5.

| | $O_2$ Flow in Step 2 (sccm) | Neck corrosion | Bottom Corrosion | At. % O | At. % Si | At. % C |
|---|---|---|---|---|---|---|
| Example 1 | 0 | 0 | 0 | 8.5 | 26 | 66 |
| Example 2 | 5 | 0 | 1 | 19 | 26 | 54 |
| Example 3 | 10 | 0 | 1 | 28 | 27 | 45 |
| Example 4 | 15 | 2 | 1 | 33 | 28 | 39 |
| Example 5 | 20 | 2 | 1 | 35 | 29 | 36 |

Containers coated using "0 sccm" oxygen in step 2 (Example 1) were measured to have a surface energy of 28 dynes/cm using a dyne fluid.

Examples 6-8

Containers were coated as specified in the aforesaid plasma treatment method, with the following exceptions: in each case Step 1 (pre-treatment with oxygen) was conducted using a plasma power 50 watts; in each case in Step 2 oxygen flow was stopped ("0 sccm"); and in Examples 7 and 8 the treatment time in Step 2 was 4 minutes or 5 minutes, respectively. The treatment time in Step 2 in Example 6 was 3 minutes.

The test for evaluation of the coating was conducted as specified in the aforesaid test procedure, with the following exceptions in each case: prior to crimping on the blind ferrule, the containers were filled with propellant 134a; crimp settings were 5.5 mm height and 17.6 mm diameter; after crimping containers were placed in a warm bath for 3 minutes at 55° C. (normal manufacturing procedure to test for leaks) and cooled in the dry-ice for 15 minutes (cooling to allow for cutting the blind ferrule off containers with propellant inside).

Table 2 summarizes the results of the corrosion examination of Examples 6 to 8

| | $O_2$ Flow in Step 2 (sccm) | Treatment time in Step 2 (min) | Neck corrosion | Bottom Corrosion |
|---|---|---|---|---|
| Example 6 | 0 | 3 | 1.3 | 0 |
| Example 7 | 0 | 4 | 1.2 | 0 |
| Example 8 | 0 | 5 | 1 | 0 |

Examples 9 to 21

In the following set of examples, the re-dispersion of salbutamol sulfate deposited & dried on the container interior surface was examined (thereby allowing an examination of salbutamol sulfate deposition/container surface characteristics) using the following method:

Two Step Deposition Test Method

1. Particle Adhesion Process 1.0 g of micronised salbutamol sulphate is dispersed in 400 g decafluoropentane available under the trade designation Vertrel XF (DuPont) and the mixture is sonicated for 3 minutes. Using a variable volume Eppendorf pipette, the 0.5 g of the resulting suspension (said aliquot containing 1.25 milligrams of salbutamol sulfate) is dispensed into three samples of each container to-be-tested and in addition three samples of a plain, uncoated container to serve as controls. The containers are then immediately placed on a horizontal rolling mixer (Stuart Scientific model SRT2) operating at 35 RPM for 10 minutes. The containers are then placed in an oven set at 50° C. for 5 minutes to complete the particle adhesion process.

2. Particle Removal Process 5 ml of decafluoropentane is added to each test container. Thereafter a blind ferrule with a gasket seal is sealed onto the can, the can is vigorously shaken for 10 vertical cycles. Fluid is discarded, and then a fresh 5 ml of decafluoropentane is added. This process is repeated a further two times, so that the process includes 4 shake & wash cycles in total.

Control containers are not subjected to the particle removal process step. All containers are then submitted for salbutamol sulphate assay by UV Spectrophotometry. Results are reported as percent of control deposition (amount of deposition on test container divided by amount of deposition on control container×100%).

Three-Step Plasma Treatment with Oxygen Post Treatment

Excluding reference examples, the containers were plasma treated similar to that described supra, however using a system provided with 16 nozzles for simultaneous treatment of 16 containers and the treatment including three steps using with the following conditions:

Step 1 Oxygen Pretreatment:

| | | |
|---|---|---|
| Oxygen flow density: | 0.16 sccm/square cm | ($O_2$ flow 100 sccm) |
| Power density: | 0.31 watts/square cm | (power 200 watts) |
| Plasma duration: | 20 seconds | |

Step 2 Diamond-Like-Glass Deposition:

| | | |
|---|---|---|
| Tetramethylsilane flow density: | 0.16 sccm/square cm | (TMS flow 100 sccm) |
| Oxygen flow rate: | zero sccm | |
| Power density: | 0.31 watts/square cm | (power 200 watts) |
| Plasma duration: | 4 minutes | |

After completion of step 2, the flow of tetramethylsilane was stopped, and a flow of oxygen was introduced to initiate a post treatment with oxygen:

Step 3—Post Deposition Treatment:

| | | |
|---|---|---|
| Oxygen flow density: | 0.16 sccm/square cm | ($O_2$ flow 100 sccm) |
| Power density: | 0.31 watts/square cm | (power 200 watts) |
| Plasma duration: | 30 seconds | |

In each step the pressure within the container was maintained within the range of 940-980 mTorr (125-130 Pa).

Over-Coating of Plasma-Deposited Oxygen-Lean Diamond-Like Glass

Selected concentrations (as shown in Table 3 in weight percent of total composition) of the following two polyfluoropolyether silanes:

$(CH_3O)_3Si(CH_2)_3N(H)C(O)$—$CF_2(CF_2CF_2O)_{9-10}$ $(CF_2O)_{9-10}CF_2$—$C(O)N(H)(CH_2)_3Si(OCH_3)_3$ (weight average molecular weight for the silane is about 2400; m and p=9-10; denoted in the following as "BI") and $C_3F_7O(CF(CF_3)CF_2O)_{5,6}CF(CF_3)$—$C(O)NH(CH_2)_3Si(OCH_3)_3$ (weight average molecular weight for the silane is about 1550; p=5.6; denoted in the following as "MONO")

were added into a liquid hydrofluoroether (HFE), a mixture of ethyl nonafluoroisobutyl ether and ethyl nonafluorobutyl ether, available under the trade designation NOVEC HFE-7200 (3M Company) to provide exemplary coating compositions.

The first listed silane (i.e., BI) was prepared as follows: $CH_3OC(O)CF_2O(CF_2CF_2O)_{9-10}(CF_2O)_{9-10}CF_2C(O)OCH_3$ (obtained from Solvay Solexis, Houston, Tex., available under the trade designation "FOMBLIN ZDEAL") (50 grams (g)) was added to an oven-dried 100-mL round bottom flask under a nitrogen atmosphere and stirred rapidly at room temperature using a magnetic stirrer. 3-Aminopropyl-trimethoxysilane (9.1 g) (obtained from GE Silicones, Wilton, Conn., available under the trade designation "SILQUEST A-1110") was added to the flask in one portion. The reaction was monitored by gas chromatography (GC) to observe excess 3-aminopropyl-trimethoxysilane and Fourier transform infrared spectroscopy (FTIR) to observe unreacted ester functional groups and was found to be complete within 90 minutes after the addition of the 3-aminopropyltrimethoxysilane. The reaction product was stirred rapidly, and the pressure in the flask was reduced to 1 mmHg (133 Pa) gradually to minimize bumping. Methanol by-product was distilled from the flask over a period of two hours, and BI was recovered from the flask.

The second listed silane (i.e., MONO) was be prepared using methods described in U.S. Pat. No. 3,250,808 (Moore) and U.S. Pat. No. 3,646,085 (Bartlett) (the contents of both documents incorporated in their entirety herein by reference). In particular the acid fluoride, $C_3F_7O(CF(CF_3)CF_2O)_{5,6}CF(CF_3)$—COF, was prepared by the polymerization of hexafluoropropylene oxide as described in U.S. Pat. No. 3,250,808 in Example XX; the acid fluoride was converted to the corresponding methyl ester via esterification, i.e., by reacting the acid fluoride with excess methanol at around 20° C. Subsequently the methyl ester was reacted with 3-aminopropyltrimethoxysilane as described in U.S. Pat. No. 3,646,085 similar to Example 2. In particular $C_3F_7O(CF(CF_3)CF_2O)_{5,6}CF(CF_3)C(O)OCH_3$ (300 g) was added to an oven-dried 1000 ml round bottom flask under a nitrogen atmosphere and stirred rapidly at 65° using a magnetic stirrer. 3-aminopropyltrimethoxysilane (44.41 g) was added to the flask in one portion. The reaction was monitored by Fourier transform infrared spectroscopy (FTIR) to observe unreacted ester functional groups as well as the formation of desired product MONO. The reaction was found to be complete after 16 hours. Methanol by-product was removed by heating in a Rotavac at 75° C. Thereafter MONO was recovered from the flask.

An aliquot of composition was placed in the plasma-coated container. For compositions including a catalyst, 2 drops of 10% dibutyl tin laurate catalyst in HFE/toluene were added to the aliquot. After the composition was placed into the container, the container was releasably closed and then shaken manually for approximately 1 minute. Thereafter excess composition in the container was removed. After this, the container was air-dried for 5 minutes, and then cured in an oven for 15 minutes at 200° C.

The containers were then tested using the Two Step Deposition Test Method and the results are summarized in Table 3

| Example No. | BI % (w/w) | MONO % (w/w) | % of Control Deposition (Avg. at least N = 3) | Standard Deviation | |
|---|---|---|---|---|---|
| 9 | — | — | 100 | 1.0 | Uncoated aluminum |
| 10 | — | — | 98.8 | 1.6 | Anodized aluminum |
| 11 | — | — | 0.8 | 0.8 | PTFE coated aluminum |
| | | | | | Over-coated plasma-treated containers: |
| 12 | 10 | — | 89.0 | 5.4 | BI (10%) |
| 13 | 9 | 1 | 48.3 | 23.8 | BI (9%) + MONO (1%) |
| 14 | 7 | 3 | 26.5 | 1.8 | BI (7%) + MONO (3%) |
| 15 | 5 | 5 | 2.9 | 2.6 | BI (5%) + MONO (5%) |
| 16 | 3 | 7 | 1.0 | 0.6 | BI (3%) + MONO (7%) |
| 17 | 1 | 9 | 0.8 | 0.3 | BI (1%) + MONO (9%) |
| 18 | 0.1 | 10 | 55.2 | 13.0 | BI (0.1%) + MONO (10%) |
| 19 | — | 11 | 79.0 | 9.5 | MONO (11%) |
| 20 | 1 | 1 | 1.7 | 1.7 | BI (1%) + MONO (1%) + catalyst |
| 21 | 5 | 5 | 0.1 | 0.2 | BI (5%) + MONO (5%) + catalyst |

Examples 22 to 24

Three-Step Plasma Treatment with $SF_6$ Post Treatment

Excluding reference examples (examples 22 & 23), containers (of example 24) were plasma treated as described supra with the following conditions:

Step 1 Oxygen Pretreatment:

| | |
|---|---|
| Oxygen flow density: | 0.32 sccm/square cm |
| Power density: | 0.47 watts/square cm |
| Plasma duration: | 20 seconds |

Step 2 Diamond-Like-Glass Deposition:

| | |
|---|---|
| Tetramethylsilane flow density: | 0.16 sccm/square cm |
| Oxygen flow rate: | zero sccm |
| Power density: | 0.47 watts/square cm |
| Plasma duration: | 3 minutes |

After completion of step 2, the flow of tetramethylsilane was stopped, and to initiate a post-fluorination-treatment on the outer-surface of the diamond-like glass coating deposited in step 2, a flow of sulfur hexafluoride was introduced:

Step 3—Post Deposition Treatment:

| | |
|---|---|
| sulfur hexafluoride flow density: | 0.32 sccm/square cm |
| Power density: | 0.31 watts/square cm |
| Plasma duration: | 30 seconds |

In the first and second step the pressure within the container was maintained at around 740 mTorr (99 Pa), and then prior to and during step 3 the pressure was lowered to about 320 mTorr (42 Pa).

Deposition of salbutamol during use of MDI canisters was examined using the following method:

Through Life Deposition Test Method

Aerosol formulation consisting of a dispersion of salbutamol sulfate particles (about 2 mg/ml) in HFA-134a was cold-filled into containers to-be-tested and 50 mcl valves commercially available under the trade designation SPRAYMISER (3M Company) were crimped onto the containers. All canisters were placed in a 55° C. water bath for 3 minutes, actuated 3 times to test valve function, and held at ambient conditions for approximately one week. The canisters were then fired down to completion (approximately 200-300 total shots), and thereafter the canisters were assayed for deposited salbutamol sulfate content. After removing from the canisters any remaining non-fired aerosol formulation, the canisters were washed with a 50 ml aliquot of solution consisting 45 parts methanol and 55 parts 0.1% (v/v) phosphoric acid in water, and the aliquot was recovered. Samples prepared from recovered aliquot and salbutamol sulfate standards were injected (20 mcl) on a Supelco C18 column (4.6 mm×150 mm; 5 mcm particles) with a mobile phase of 45% methanol and 55% 100 mM triethylamine phosphate with 5 mM sodium dodecyl sulfate pH 2.5 and a flow rate of 2 ml/minute. The analysis time was 6 minutes and the salbutamol peak was quantified by UV absorbance at 225 nm. Results are reported in mcg/container and summarized in Table 4.

| Example | MDI Canister Type | Salbutamol Sulfate Deposition - mcg/can (Average of N = 5) | Standard Deviation mcg/can |
|---|---|---|---|
| 22 | Uncoated Aluminum | 1283 | 149 |
| 23 | Anodized Aluminum | 1215 | 275 |
| 24 | $SF_6$ plasma treated | 568 | 126 |

The invention claimed is:
1. A method of making a medicinal inhalation device or a component of a medicinal inhalation device comprising:
   forming by plasma deposition under ion bombardment conditions a non-metal coating on at least a portion of a surface of the device or the component, respectively, wherein the non-metal coating formed is a diamond-like glass comprising hydrogen and on a hydrogen free basis from about 20 to, but not including 40 atomic percent of silicon, greater than 60 atomic percent of carbon, and less than 15 down to and including zero atomic percent of oxygen; and
   applying to at least a portion of a surface of the non-metal coating a composition comprising an at least partially fluorinated compound that is a polyfluoropolyether silane of Formula Ia:

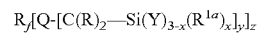

$$R_f[Q\text{-}[C(R)_2\text{—}Si(Y)_{3-x}(R^{1a})_x]_y]_z \quad \text{Ia}$$

wherein:
   $R_f$ is a monovalent or multivalent polyfluoropolyether segment;
   Q is an organic divalent or trivalent linking group;
   each R is independently hydrogen or a $C_{1-4}$ alkyl group;
   each Y is independently a hydrolyzable group;
   $R^{1a}$ is a $C_{1-8}$ alkyl or phenyl group;
   x is 0 or 1 or 2;
   y is 1 or 2; and
   z is 1, 2, 3, or 4.

2. A method according to claim 1, wherein, on a hydrogen free basis, the content of oxygen in the diamond-like glass is zero up to and including about 12 atomic percent.

3. A method according to claim 1, wherein prior to forming the non-metal coating, said surface of the device or the component, is exposed to an argon plasma.

4. A method according to claim 1, wherein the method further comprises a step of:
exposing at least a portion of a surface of the formed non-metal coating to a fluorine-containing-gas plasma under ion bombardment conditions.

5. A method according to claim 1, wherein said at least partially fluorinated compound comprises at least one functional group and said non-metal coating has at least one functional group, wherein the non-metal coating is provided with said at least one functional group during the forming step or after the forming step the formed non-metal coating is treated to provide the non-metal coating with said at least one functional group, and wherein the method further comprises a step of:
allowing at least one functional group of the at least partially fluorinated compound to react with at least one functional group of the non-metal coating to form a covalent bond.

6. A method according to claim 1, wherein the composition comprising an at least partially fluorinated compound further comprises an organic solvent.

7. The method of claim 6, wherein the organic solvent is a fluorinated solvent.

8. A method according to claim 1, wherein the composition comprising an at least partially fluorinated compound further comprises water and a non-fluorinated cross-linking agent.

9. The method of claim 8, wherein the cross-linking agent comprises one or more non-fluorinated compounds, each compound having at least two hydrolyzable groups per molecule.

10. A method according to claim 1, wherein the method is free of a step of applying a fluorine-containing over-coating or a fluorine-containing surface-treatment onto the surface of the non-metal coating.

11. A method according to claim 1, where said surface of the device or said surface of the component of the device, as applicable, is a surface that is or will come in contact with a medicament or a medicinal formulation during storage or delivery from the medicinal inhalation device.

12. A method according to claim 1, where said surface of the device or said surface of the component of the device, as applicable, is a surface that comes in contact with a movable component of the device or is a surface of a movable component of the device.

13. A method according to claim 1, where said medicinal inhalation device is a metered dose inhaler or a dry powder inhaler.

14. A medicinal inhalation device or a component of a medicinal inhalation device made according to claim 1.

15. A medicinal inhalation device or a component of a medicinal inhalation device comprising:
a diamond-like glass coating on at least a portion of a surface of the device or the component, respectively, said diamond-like glass comprising hydrogen and on a hydrogen free basis about 20 to, but not including 40 atomic percent of silicon, greater than 60 atomic percent of carbon, and less than 15 down to and including zero atomic percent of oxygen; and
a composition applied to at least a portion of a surface of the non-metal coating, the composition comprising an at least partially fluorinated compound that is a polyfluoropolyether silane of Formula Ia:

$$R_f[Q-[C(R)_2-Si(Y)_{3-x}(R^{1a})_x]_y]_z \qquad \text{Ia}$$

wherein:
$R_f$ is a monovalent or multivalent polyfluoropolyether segment;
Q is an organic divalent or trivalent linking group;
each R is independently hydrogen or a $C_{1-4}$ alkyl group;
each Y is independently a hydrolyzable group;
$R^{1a}$ is a $C_{1-8}$ alkyl or phenyl group;
x is 0 or 1 or 2;
y is 1 or 2; and
z is 1, 2, 3, or 4.

* * * * *